(12) United States Patent
Zhao et al.

(10) Patent No.: US 11,898,270 B2
(45) Date of Patent: Feb. 13, 2024

(54) PIG GENOME-WIDE SPECIFIC SGRNA LIBRARY, PREPARATION METHOD THEREFOR AND APPLICATION THEREOF

(71) Applicant: HUAZHONG AGRICULTURAL UNIVERSITY, Hubei (CN)

(72) Inventors: Shuhong Zhao, Hubei (CN); Shengsong Xie, Hubei (CN); Changzhi Zhao, Hubei (CN); Xinyun Li, Hubei (CN); Xiangdong Liu, Hubei (CN); Xiaosong Han, Hubei (CN); Gaojuan Yang, Hubei (CN); Yang Gao, Hubei (CN); Yilong Chen, Hubei (CN); Xiaoyong Du, Hubei (CN); Yiliang Miao, Hubei (CN); Yunlong Ma, Hubei (CN); Xiaolei Liu, Hubei (CN)

(73) Assignee: HUAZHONG AGRICULTURAL UNIVERSITY, Hubei (CN)

( * ) Notice: Subject to any disclaimer, the term of this patent is extended or adjusted under 35 U.S.C. 154(b) by 0 days.

(21) Appl. No.: 16/628,481

(22) PCT Filed: Aug. 21, 2017

(86) PCT No.: PCT/CN2017/098324
§ 371 (c)(1),
(2) Date: Apr. 3, 2020

(87) PCT Pub. No.: WO2019/006833
PCT Pub. Date: Jan. 10, 2019

(65) Prior Publication Data
US 2020/0325597 A1 Oct. 15, 2020

(30) Foreign Application Priority Data
Jul. 3, 2017 (CN) .......................... 201710533398.9

(51) Int. Cl.
| | |
|---|---|
| C12N 15/90 | (2006.01) |
| C40B 40/02 | (2006.01) |
| C12N 9/22 | (2006.01) |
| C12N 15/113 | (2010.01) |
| C12N 15/85 | (2006.01) |
| C12Q 1/6869 | (2018.01) |
| C40B 40/06 | (2006.01) |
| C40B 50/06 | (2006.01) |

(52) U.S. Cl.
CPC ................ *C40B 40/02* (2013.01); *C12N 9/22* (2013.01); *C12N 15/113* (2013.01); *C12N 15/85* (2013.01); *C12N 15/907* (2013.01); *C12Q 1/6869* (2013.01); *C40B 40/06* (2013.01); *C40B 50/06* (2013.01); *C12N 2810/10* (2013.01)

(58) Field of Classification Search
None
See application file for complete search history.

(56) References Cited

FOREIGN PATENT DOCUMENTS

| | | |
|---|---|---|
| CN | 103668472 A | 3/2014 |
| WO | 2016197358 | * 12/2016 |

OTHER PUBLICATIONS

Cai et al (WO2016/197358) partial English translation (Year: 2016).*
Emmanouil Metzakopian et al., Enhancing the genome editing toolbox: genome wide CRISPR arrayed libraries, Scientific Reports, May 22, 2017, pp. 1-9.
Shengsong Xie et al., sgRNA design for the CRISPR/Cas9 system and evaluation of its off-target effects, Hereditas, Aug. 4, 2015, pp. 1125-1139, Considered to the extent of the English Abstract.
Hiroko Koike-Yusa et al., Genome-wide recessive genetic screening in mammalian cells with a lentiviral CRISPR-guide RNA library, nature biotechnology, Dec. 23, 2013, pp. 267-276.
Changzhi Zhao et al., Defelopment of a graphical user interface for sgRNAcas9 and its application, Chinagene, Sep. 8, 2015, pp. 1061-1072, Considered to the extent of the English Abstract.

* cited by examiner

*Primary Examiner* — Christopher M Gross
(74) *Attorney, Agent, or Firm* — NKL Law; Allen Xue

(57) ABSTRACT

Provided is a pig genome-wide specific sgRNA library, a preparation method therefor, and an application thereof. The sgRNA is targeted at a pig genome-wide protein-coding gene, lincRNA and/or miRNA. Specifically, an sgRNA construct has the following structure: AL-N20-AR, wherein AL is the left homology arm sequence located at the upstream of the coding sequence of a pig specific SgRNA, N20 is the coding sequence of the pig specific SgRNA, and AR is a right homology arm sequence located at the downstream of the coding sequence of the pig specific sgRNA. The sgRNA library can be used for screening functional genes of a pig or for preparing a kit.

8 Claims, 17 Drawing Sheets
Specification includes a Sequence Listing.

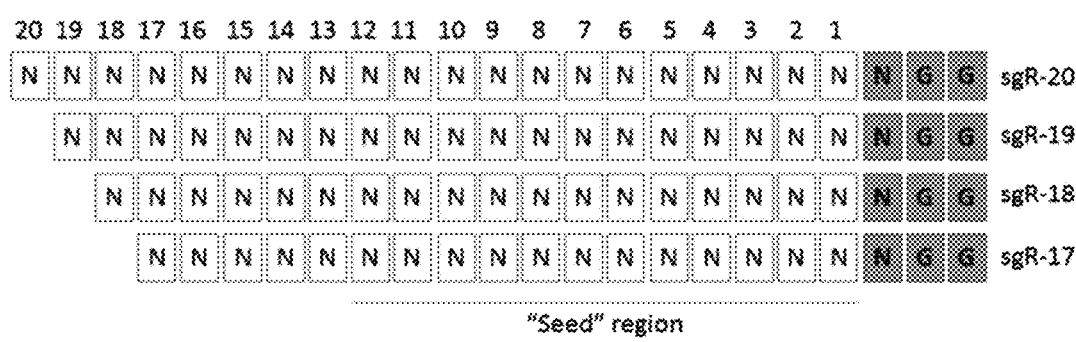
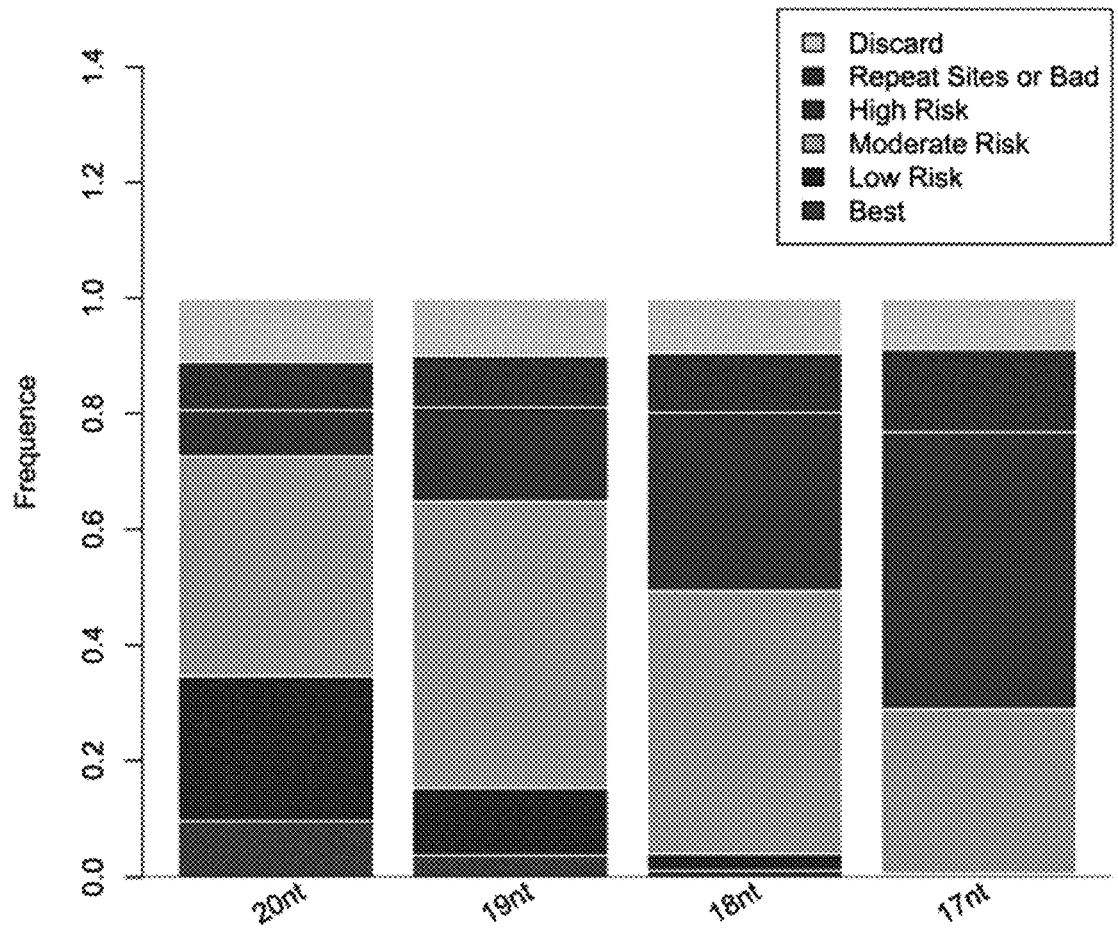
--- The abscissa indicates the sgRNA length
---The ordinate indicates the predicted frequency of off-target risks of different types
FIG. 1

--- The abscissa indicates the sgRNA length
--- The ordinate indicates the predicted number of off-target sites Note:
Column 1: sgRNA number
Column 2: sgRNA target sequence
Column 3: sgRNA length
Column 4: GC% content of sgRNA
Columns 5-10: sgRNA target or predict number of off-target sites
Column 11: total number of sgRNA predicted off-target sites Note: T7EN1, which means the efficiency of genome editing is evaluated by T7EN1 digestion experiment AmpliconSeq, which evaluates genome editing efficiency through amplicons and high-throughput sequencing

A

| ID | Off-target sequence(5'-3') | AR-17-sgR | | AR-18-sgR | | AR-19-sgR | | AR-20-sgR | |
|---|---|---|---|---|---|---|---|---|---|
| | | No.of Mms | Cleave efficiency(%) | No.of Mms | Cleave efficiency(%) | No.of Mms | Cleave efficiency(%) | No.of Mms | Cleave efficiency(%) |
| On-target | GGAAGGTGGCAGCTGCTGCGG | 0 | 12.2 | 0 | 17.3 | 0 | 20 | 0 | 28.3 |
| POT-1 | GcAaGcaCTGgCAGCTGCTGCGG | 3 | 0 | 3 | 0 | 4 | 0 | 4 | 0 |
| POT-2 | GatGGctTTGgCAGcAGCTGCTGCGG | 3 | 0 | 4 | 0 | 5 | 0.1 | 5 | 0 |
| POT-3 | GGtGcaGGCTGgCAGCTGCTGCGG | 2 | 3.1 | 3 | 1.3 | 3 | 1.2 | 3 | 1.3 |
| POT-4 | tGtGGaGGTTgCAGCTGCTGCGG | 1 | 3.9 | 2 | 2 | 2 | 5.3 | 3 | 12.2 |
| POT-5 | GGAGaaGGTagCAGCTGCTGCGG | 3 | 1 | 3 | 2.3 | 3 | 2.9 | 3 | 1.5 |
| POT-6 | aGTacTGCTggCAGCTGCTGCGG | 2 | 1.1 | 2 | 0.8 | 2 | 0.2 | 3 | 0.7 |
| POT-7 | aGAGGTGCTgGCAGCTGCTGCGG | 1 | 3.5 | 1 | 7.1 | 1 | 27.1 | 2 | 28.3 |
| POT-8 | GGAaGgGtCTGGCAGCTGCTGCGG | 3 | 0 | 3 | 0.4 | 3 | 0 | 3 | 0.8 |
| POT-9 | GGAGaCTGCTtGCAGCTGCTGCGG | 1 | 1.3 | 1 | 1.7 | 1 | 1.8 | 1 | 4.2 |
| POT-10 | GGtaGTaCTgGCAGCTGCTGCGG | 2 | 8.6 | 3 | 0 | 3 | 1.3 | 3 | 0 |
| POT-11 | GGAGGcCTgGCAGCTGCTGCGG | 2 | 5.7 | 2 | 1.5 | 2 | 2.1 | 2 | 4.1 |
| POT-12 | GGAtGtgTtGCACAGCTGCTGCGG | 2 | 5.8 | 2 | 3.3 | 2 | 2 | 2 | 0 |
| POT-13 | GagcGgGCTGGCAGCTGCTGCGG | 2 | 2.1 | 3 | 1.4 | 4 | 2.9 | 4 | 0.4 |
| POT-14 | tcTcGGTgTGGCAGCTGCTGCGG | 1 | 0.3 | 2 | 0.8 | 2 | 1.1 | 3 | 0.2 |
| POT-15 | cGGctGTGCTGgCAGCTGCTGCGG | 1 | 11.6 | 2 | 0 | 2 | 9.8 | 3 | 2.8 |
| POT-16 | GGtGGTgGTgGCAGCTGCTGCGG | 1 | 1.5 | 3 | 1.3 | 2 | 0.7 | 2 | 4.7 |
| POT-17 | GtgttTGCTgGCAGCTGCTGCGG | 2 | 0.7 | 2 | 0.8 | 4 | 0.9 | 4 | 0.5 |
| POT-18 | aGcaGgGaTTagCAGCTGCTGCGG | 1 | 5.8 | 2 | 7.4 | 2 | 3.7 | 3 | 7.7 |
| POT-19 | tctcGTGcTGTtGCAGCTGCTGCGG | 1 | 3.9 | 2 | 1.2 | 3 | 1.7 | 4 | 1.9 |

Note: POT indicates the predicted off-target site, No. of Mms indicates the number of off-target bases, and Cleave efficiency (%) indicates the cutting efficiency.

B

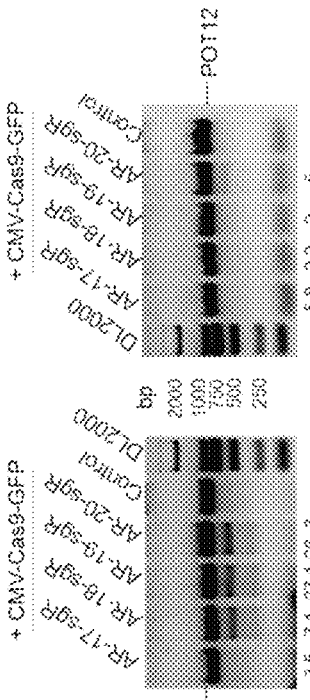

FIG. 5

High-throughput sequencing analysis of oligodeoxynucleotide pools synthesized in porcine whole genome sgRNAs (PigGeCKO)

|  | complete matching | | with 3 base mismatches | |
| --- | --- | --- | --- | --- |
|  | probe full-length sequence | 20 nt sgRNA | probe full-length sequence | 20 nt sgRNA |
| amount | 85674 | 85674 | 85674 | 85674 |
| alignment success | 85014 (99.23%) | 85439 (99.73%) | 85122 (99.36%) | 85517 (99.82%) |
| no alignment | 660 (0.77%) | 235 (0.27%) | 552 (0.64%) | 157 (0.18%) |

FIG. 7

T4 DNase ligated transformed clone statistics:

| PCR product content for library construction (ng) | T4 Ligase ligation reaction product (µL) | total number of clones |
| --- | --- | --- |
| 1 | 10 | $2.5 \times 10^5$ |
| 5 | 10 | $3 \times 10^5$ |
| 10 | 10 | $1 \times 10^5$ |
| 50 | 10 | $0.37 \times 10^5$ |

FIG. 8 clone statistics of 5 μl of Gibson assembly solution transformed one plate

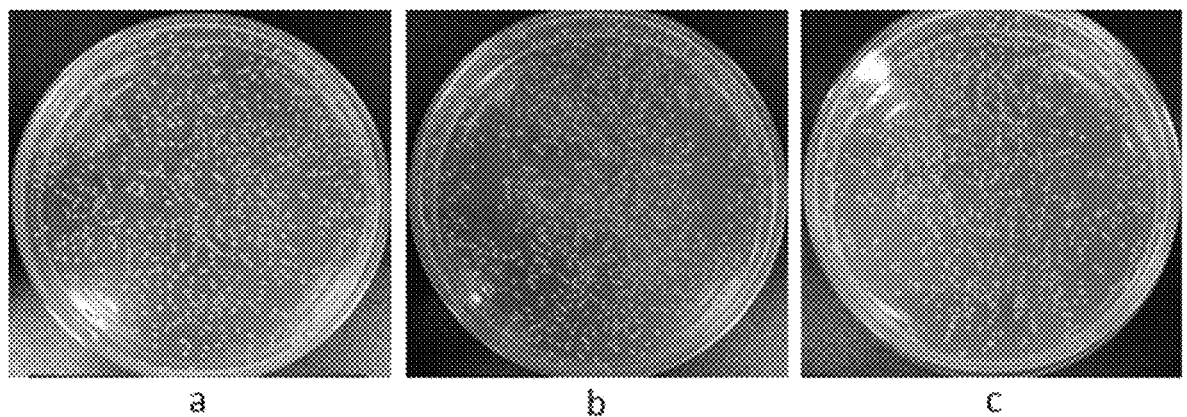

a  b  c clone statistics of 20 μL Gibson assembly solution for the chemical transformation

| Numbering | Amount of library amplification purification product used for one ligation reaction (ng) | Gibson assembly products for a transformation reaction (μl) | Total number of clones |
|---|---|---|---|
| a | 60 | 5 | $\geq 2.3 \times 10^4$ |
| b | 60 | 10 | $\geq 1.7 \times 10^4$ |
| c | 60 | 20 | $\geq 5.5 \times 10^3$ |

FIG. 10 clone statistics of 5 µl of Gibson assembly solution transformed one plate

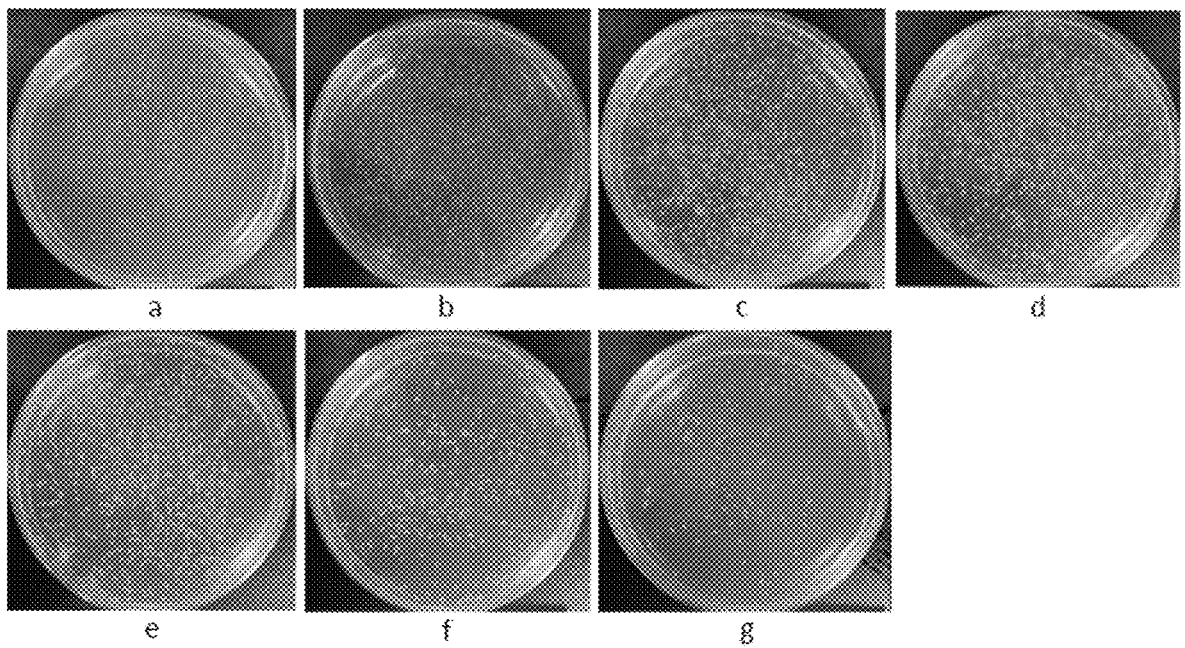

20µl Gibson assembly solution transformed clone statistics

| Numbering | amount of library amplification purification product used for one ligation reaction (ng) | Gibson assembly products used for a transformation reaction (µL) | Total number of clones |
|---|---|---|---|
| a | 5 | 5 | $\geq 6 \times 10^4$ |
| b | 10 | 5 | $\geq 10 \times 10^4$ |
| c | 20 | 5 | $\geq 2.8 \times 10^4$ |
| d | 50 | 5 | $\geq 2.5 \times 10^4$ |
| e | 100 | 5 | $\geq 2.1 \times 10^4$ |
| f | 200 | 5 | $\geq 8.4 \times 10^3$ |
| g | 450 | 5 | $\geq 3.5 \times 10^3$ |

FIG. 11

| target name | Comment | sgRNA name | sequence (5'-3') | sgRNA activity score | GC% | Total predicted off-target bases | Note |
|---|---|---|---|---|---|---|---|
| ENSSSCG00000000001 | CELSR1 | CELSR1-1 | TCACGACTGGCGCCACCACCAGGG | 0.760116007 | 69.6 | 6 | mRNA |
| ENSSSCG00000000001 | CELSR1 | CELSR1-2 | CGTTCCACTCCATGCTCACTCACGG | 0.750724238 | 69.6 | 0 | mRNA |
| ENSSSCG00000000001 | CELSR1 | CELSR1-3 | AGGTTCGCAACATCGATCCGTGGG | 0.749038212 | 69.6 | 1 | mRNA |
| ENSSSCG00000000003 | TTC38 | TTC38-1 | GATTTCACATCTTCGCCACGG | 0.758472147 | 56.5 | 5 | mRNA |
| ENSSSCG00000000003 | TTC38 | TTC38-2 | TCCCGTGCCAATCACCACAAGG | 0.618077427 | 65.2 | 10 | mRNA |
| ENSSSCG00000000003 | TTC38 | TTC38-3 | CGGATGTCAAGTGTCCAGAATGG | 0.490863943 | 60.9 | 17 | mRNA |
| ENSSSCG00000000004 | PKDREJ | PKDREJ-1 | GGACAGCCTCGAACCCCACAGGG | 0.766240913 | 69.6 | 9 | mRNA |
| ENSSSCG00000000004 | PKDREJ | PKDREJ-2 | GGAACTGACGTCAACTCTACGG | 0.75043184 | 60.9 | 6 | mRNA |
| ENSSSCG00000000004 | PKDREJ | PKDREJ-3 | GCTGGGCGACACGGTCGGAGGCGG | 0.695086823 | 78.3 | 6 | mRNA |
| ALDBSSCT00000000002 | | ALDBSSCT00000000002-1 | CTTCTACATACCAGACCACGAGG | 0.892844928 | 56.5 | 2 | lincRNA |
| ALDBSSCT00000000002 | | ALDBSSCT00000000002-2 | CCAACTTTCCTTCCGCATCGG | 0.717293079 | 65.2 | 4 | lincRNA |
| ALDBSSCT00000000002 | | ALDBSSCT00000000002-3 | CTCTGTATGTAGAGATCCGTGG | 0.46722269 | 56.5 | 7 | lincRNA |
| ENSSSCT00000019722 | | ENSSSCT00000019722-1 | GRAATTCACAATCTCCAACAGG | 0.351230972 | 52.2 | 13 | miRNA |
| ENSSSCT00000019722 | | ENSSSCT00000019722-2 | TGAGTACGGCCATGTGTCTGTTGG | 0.14955378 | 56.5 | 2 | miRNA |
| ENSSSCT00000019722 | | ENSSSCT00000019722-3 | CAATTCTAACAGGACATCGTGG | 0.141313853 | 56.5 | 6 | miRNA |
| ENSSSCT00000019781 | | ENSSSCT00000019781-1 | CTTAGACAGCCCAGCTTAGCCG | 0.456652708 | 65.2 | 9 | miRNA |
| ENSSSCT00000019781 | | ENSSSCT00000019781-2 | GCTTGGCGGTTGAGGAATGGG | 0.207673858 | 65.2 | 12 | miRNA |
| ENSSSCT00000019781 | | ENSSSCT00000019781-3 | TTCCTCCAACCGTCCAAGCTTGG | 0.126913052 | 65.2 | 6 | miRNA |
| ntc | | ntc-1 | TTTACGTAGATCGAACAACGCGGGG | 0.964174041 | 56.5 | 0 | nonsense sgRNA |
| ntc | | ntc-2 | TGAGTTTGCCAATATCACCCGGGG | 0.940704143 | 52.2 | 0 | nonsense sgRNA |
| ntc | | ntc-3 | GTACATCGATAGAATTCGATCGG | 0.929195354 | 52.2 | 0 | nonsense sgRNA |

FIG. 16

PIG GENOME-WIDE SPECIFIC SGRNA LIBRARY, PREPARATION METHOD THEREFOR AND APPLICATION THEREOF

INCORPORATION OF SEQUENCE LISTING

This application contains a sequence listing submitted in Computer Readable Form (CRF). The CFR file containing the sequence listing entitled "PB4083701_ST25.txt", which was created on Feb. 27, 2023, and is 40,563 bytes in size. The information in the sequence listing is incorporated herein by reference in its entirety.

TECHNICAL FIELD

The present invention belongs to the field of biotechnology. Specifically, it is related to a method for designing and constructing the porcine whole genome CRISPR/Cas9 knockout library.

BACKGROUND OF THE INVENTION

The high-throughput screening of functional genes using loss-of-function and gain-of-function strategies is the main method for quick identification of important or key genes that regulate specific phenotypes. Traditional genetic screening methods using RNA interference libraries have advantages such as simple operation and relatively low cost, although they have been widely used, their disadvantages such as incomplete inhibition and obvious off-target effects still exist.

The CRISP/Cas9 technology, which has emerged in recent years, can quickly, easily, and accurately implement editing functions such as genome knockout, thus becoming a powerful genetic screening tool.

In a variety of cell lines, human, mouse, zebrafish and other model animals, large-scale application of this method to screen functional genes has achieved some great successes.

However, no report is available about the porcine whole genome CRISPR/Cas9 knockout library.

Therefore there is an urgent need in the art to develop a method of designing a sgRNA for porcine whole genome protein-coding genes, lincRNA, and miRNA, thereby constructing a CRISPR/Cas9 lentiviral knockout library, which can be used to achieve a high-throughput screening of porcine functional genes.

SUMMARY OF THE INVENTION

The aim of the present invention is to provide a method of designing a sgRNA for porcine whole genome protein-coding genes, lincRNA, and miRNA, thereby constructing a CRISPR/Cas9 lentiviral knockout library, which can be used to achieve a high-throughput screening of porcine functional genes.

In the first aspect of the present invention, it provides a porcine whole genome-specific sgRNA library, including:
(i) N kinds of vectors expressing porcine-specific sgRNA, wherein N is a positive integer ≥20,000, the porcine-specific sgRNA is a target gene for the porcine whole genome and the target gene is selected from the group consisting of: (a) a protein encoding gene, (b) lincRNA, (c) miRNA, (d) the combination of (a), (b) and (c);
in addition, the porcine-specific sgRNA has the following structural characteristics:

(1) the target gene locus targeted by the sgRNA contains PAM as NGG (N is any base of A, T, C, G)
(2) the length of sgRNA is 19 or 20 nt.
(3) the GC content of sgRNA is 40-60%.
(4) the whole-genome off-target evaluation of sgRNA selects off-target sites that do not contain 1 and 2 base mismatches, compared with other sgRNAs, sgRNAs with a relatively small number of off-targets are selected;
(5) for a porcine-specific sgRNA that targets a protein-coding gene, the binding position thereof is located in a region 500 bp downstream of the start codon ATG of the coding gene; for a porcine-specific sgRNA that targets a lincRNA gene, the binding position thereof is located in a 500 bp region downstream of the lincRNA transcription start point; for a porcine-specific sgRNA that targets a miRNA gene, the binding position thereof is a miRNA precursor sequence or a mature sequence; and (ii) optionally, M kinds of negative control vectors, which are the vectors expressing unrelated sgRNA (nonsense sgRNA), wherein M is a positive integer.

Preferably, the sequence of the sgRNA is characterized by $N_{20}NGG$ (N is any base of A, T, C, Preferably, N is from 30,000 to 150,000, more preferably from 40,000 to 100,000, and most preferably from 60,000 to 90,000.

Preferably, M is from 10 to 10,000, preferably from 50 to 5,000, more preferably from 200 to 3,000, and most preferably from 500 to 2,000.

Preferably, in the library, the N kinds of porcine-specific sgRNAs target ≥90% (preferably ≥95%, more preferably 96-100% or 96-99%) of porcine protein-encoding genes.

Preferably, in the library, the N kinds of porcine-specific sgRNAs target ≥90% (preferably ≥95%, more preferably 96-100% or 96-99%) of porcine lincRNAs.

Preferably, in the library, the N kinds of porcine-specific sgRNAs target ≥90% (preferably ≥95%, more preferably 96-100% or 96-99%) of porcine miRNAs.

Preferably, the average coverage depth of the porcine-specific sgRNAs for all genes of the porcine whole genome is 2-10, more preferably 2-6, and most preferably 2-4, i.e., there are on average 3 or 3 kinds of porcine-specific sgRNAs for each gene.

Preferably, the term "vector" includes an expression vector.

Preferably, the vector is selected from the group consisting of: plasmids, viral vectors, and a combination thereof.

Preferably, the viral vector includes a lentiviral expression vector, an adenovirus expression vector, a transposon expression vector, and a combination thereof.

Preferably, the expression vector contains elements expressing Cas9 or sgRNA as well as lentivirus, adenovirus, and transposon; Preferably, the expression vector contains a kit for expressing a porcine sgRNA, with a structure from 5' to 3' as shown in Formula I:

$$Z0\text{-}Z1\text{-}Z2 \tag{I}$$

wherein
Z0 is a first promoter;
Z1 is AL-N20-AR, wherein AL is a left arm sequence upstream of the coding sequence of porcine-specific sgRNA; N20 is a coding sequence of porcine-specific sgRNA; AR is a right arm sequence downstream of the coding sequence of porcine-specific sgRNA;
Z2 is a sgRNA scaffold sequence.

Preferably, the expression cassette has the structure from 5' to 3' as shown in Formula II:

Z0-Z1-Z2-L-Z3-Z4 (II)

wherein Z0, Z1, and Z2 are as described above;
L indicates an optional interval sequence;
Z3 is a second promoter;
Z4 is a reporter gene.

Preferably, AL is an additional forward primer binding sequence containing a restriction endonuclease site.

Preferably, AL is a left-sided homologous vector sequence next to upstream of the restriction endonuclease cleavage site after the linearization of the sgRNA expression vector by restriction endonuclease.

Preferably, AR is an additional reverse primer binding sequence containing a restriction endonuclease site.

Preferably, AR is a right-sided homologous vector sequence next to downstream of the restriction endonuclease cleavage site after the linearization of the sgRNA expression vector by restriction endonuclease.

Preferably, the length of AL is 25-40 bp, and more preferably 25-35 bp.

Preferably, the length of N20 is 20 nt.

Preferably, the length of AR is 25-40 bp, and more preferably 28-35 bp.

Preferably, the first promoter is the one that initiates sgRNA expression.

Preferably, the first promoter is selected from the group consisting of: a U6 promoter, a drug-inducible promoter (such as Tet on/off system), and a combination thereof.

Preferably, the second promoter is selected from the group consisting of: a CMV promoter, a CAG promoter, a CBh promoter, a tissue-specific promoter, and a combination thereof.

Preferably, the reporter gene is selected from the group consisting of: Neomycin, Puromycin, RFP, EGFP, mCherry, Blasticidin, and a combination thereof.

Preferably, the expression vector is selected from the group consisting of: PX330, lenti-sgRNA-EGFP, Adv-sgRNA, AAV-sgRNA, PB (pigsgy Bac)-sgRNA, and a combination thereof.

Preferably, Z1 has a structure of Formula (IV):
5'-TATCTTGTGGAAAGGACGAAACACCG (SEQ ID NO.: 163)
$N_{20}$GTTTTAGAGCTAGAAATAGCAAGTTAAAAT (SEQ ID NO.: 164)-3' (IV)
wherein $N_{20}$ is a coding sequence for a porcine-specific sgRNA.

Preferably, the sgRNA library has a capacity of 82,392 porcine specific sgRNAs.

Preferably, the library is prepared by the method according to the second aspect of the present invention.

In the second aspect of the present invention, it provides a method for preparation of the porcine whole genome-specific sgRNA library according to the first aspect of present invention, comprising the steps of:
(a) providing a nucleic acid construct Z1, which has the following structure:

AL-$N_{20}$-AR wherein AL is a left homologous arm sequence upstream of the coding sequence of the porcine-specific sgRNA;
$N_{20}$ is a coding sequence of a porcine-specific sgRNA;
AR is a right homologous arm sequence downstream of the coding sequence of the porcine-specific sgRNA.

(b) using the nucleic acid construct Z1 as a template to perform PCR amplification to obtain an amplification product;
(c) mixing the amplification product with a linearized expression vector and using a Gibson assembly method to ligate, thereby forming a ligation product;
(d) transforming the ligation product into E. coli to obtain a transformant;
(e) extracting a plasmid from the transformant, thereby obtaining the porcine whole genome-specific sgRNA library.

Preferably, the method further includes:
(f) the plasmid is introduced into cells for producing virus, thereby generating viral particles (viral vector).

Preferably, the virus includes a lentivirus and/or adenovirus.

Preferably, in step (a), there are N1 kinds of nucleic acid constructs Z1, wherein N1 is a positive integer ≥20,000.

Preferably, N1 is from 30,000 to 150,000, more preferably from 40,000 to 100,000, and most preferably from 60,000 to 90,000.

Preferably, the nucleic acid construct Z1 has a structure of Formula (IV).

Preferably, in the step (c), the primer for PCR amplification is as follows:

(SEQ ID NO.: 130)
F: 5'-GGCTTTATATATCTTGTGGAAAGGACGAAACACCG-3', (SEQ ID NO.: 131)
R: 5'-CTAGCCTTATTTTAACTTGCTATTTCTAGCTCTAAAAC-3'.

Preferably, in step (c), the linearized expression vector is produced by digestion with BbsI.

Preferably, the expression vector is selected from the group consisting of: PX330, lenti-sgRNA-EGFP, Adv-sgRNA, AAV-sgRNA, PB (pigsgy Bac)-sgRNA, and a combination thereof.

Preferably, the expression vector is lenti-sgRNA-EGFP.

Preferably, the method further includes:
(g) infecting the porcine cells with the virus vector under low MOI conditions (e.g., 0.1-0.8, preferably 0.2-0.4).

Preferably, in step (g), each porcine cell is essentially infected with one viral vector (or virion).

Preferably, the porcine cell is selected from the group consisting of: porcine PK-15 cell, 3D4/21 cell, and a combination thereof.

In the third aspect of the present invention, it provides a kit, which includes:
(a) a first container and a porcine whole genome-specific sgRNA library according to the first aspect of the present invention located in the container.
(b) instructions, which describes the instructions of the porcine whole genome-specific sgRNA library.

Preferably, the kit further includes:
(c) a second container and a porcine cell located in the container, the porcine cell contains a constitutive or inducible Cas9 protein expression.

Preferably, the porcine cell is selected from the group consisting of: porcine PK-15 cell, 3D4/21 cell, and a combination thereof.

In the fourth aspect of the present invention, it provides a use of the sgRNA library according to the first aspect of the present invention for the preparation of a kit for high throughput screening of a porcine functional gene or for the screening of porcine functional genes.

Preferably, the functional gene is selected from the group consisting of: a protein coding gene, a lincRNA, a miRNA, and a combination thereof.

Preferably, the screening is involved in a non-therapeutic and non-diagnostic method.

It is to be understood that, within the scope of this invention, the above-described technical features of the present invention and the technical features specifically described in the following (e.g., embodiments) can be combined with each other to form a new or preferred technical solution. Due to space limitations, they are not repeated here.

BRIEF DESCRIPTION OF THE FIGURES

FIG. 5. Verification of 19 off-target sites randomly selected for targeting AR genes in Example 1 of the present invention.

FIG. 7. High-throughput sequencing analysis of an oligonucleotide pool for porcine whole genome sgRNA synthesis in Example 3 of the present invention.

FIG. 8. Comparison of the effect of the content of the PCR product used to construct the library on the growth of the number of clones after ligation in Example 3 of the present invention.

FIG. 10. Comparison of the effect of different amounts of Gibson assembly products on the growth of clones in a transformation reaction in Example 3 of the present invention.

FIG. 11. Comparison of the effects of the amount of amplifying and purifying products from different libraries on the growth of clones in a ligation reaction in Example 5 of the present invention.

FIG. 16. An example for designing the porcine whole genome CRISPR/Cas9 knockout library.

DETAILED DESCRIPTION OF THE INVENTION

Figure 1:
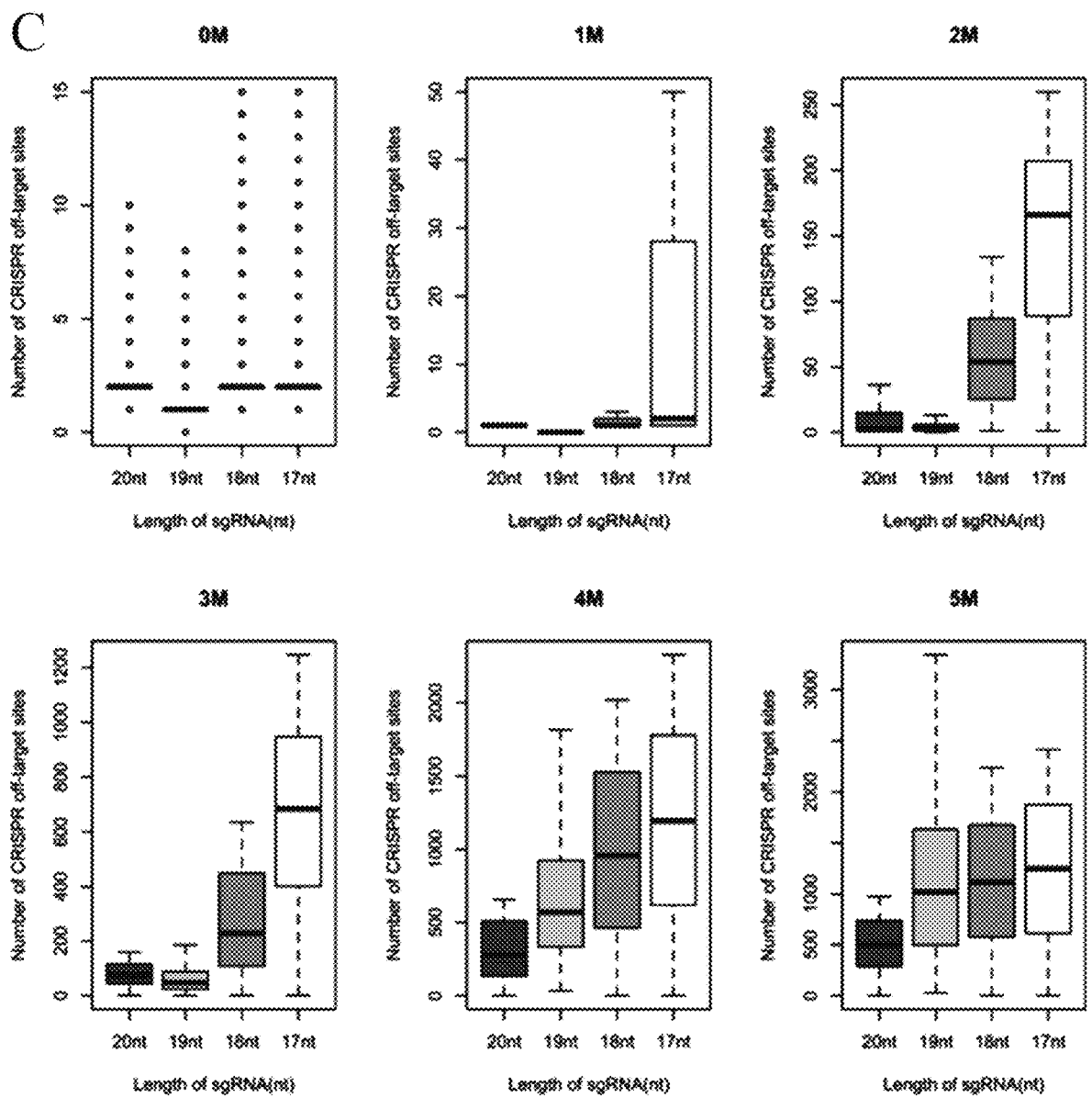
FIG. 1 is an is an off-target risk assessment of a 17 nt, 18 nt, 19 nt and 20 nt of sgRNAs in Example 1 of the present invention. A. The schematic diagram of sgRNAs with a different length; B. using sgRNAcas9 software to design sgRNAs for 100 genes and compare off-target analysis of sgRNAs with different lengths. C. Comparison of mismatched bases of off-target sites of sgRNAs with a different length.

Through extensive and in-depth research, the inventors have developed a method of designing a sgRNA for porcine whole genome protein-coding genes, lincRNA, and miRNA, thereby constructing a CRISPR/Cas9 lentiviral knockout library, which can be used to achieve a high-throughput screening of porcine functional genes. On this basis, the inventors have completed the present invention.

Specifically, the present invention has developed a porcine whole genome CRISPR/Cas9 knockout library plasmid kit. The kit contains a Cas9 expression vector and 82,392 sgRNA expression vector libraries which target 14,958 coding genes, 14,168 lincRNAs and 142 miRNAs of pig. It also contains 970 negative control sgRNAs and a PK-15 cell line stably expressing Cas9, which can be used in combination for high-throughput screening of porcine functional genes at the genome-wide level.

Terminology

As used herein, the term "plasmid" may refer to an expression vector, when it is transferred into a cell, it can express the coding sequence or non-coding sequence linked to a promoter contained therein. The plasmid usually contains the components necessary for gene expression. In the present invention, the plasmid used may be a eukaryotic gene expression plasmid, a lentiviral vector plasmid, or any other plasmid that can express a coding or non-coding gene contained therein, preferably a lentiviral vector plasmid.

As used herein, the term "Gibson Assembly", also known as Gibson Assembly®, was proposed in 2009 by Dr. Daniel Gibson from the J. Craig Venter Institute. The Gibson assembly method can not only splice multiple linear DNA fragments and but also insert the target DNA into a vector. When performing Gibson assembly, homologous fragments are first added to the ends of the DNA fragments, followed by incubation with the master mix for 1 hour. The master mix consists of three enzymes, with the DNA exonuclease first degraded nucleotides from the 5' end to produce cohesive ends, then, the overlapping sequences between adjacent fragments are annealed. Finally, the DNA polymerase and DNA ligase fill the sequence to form a complete double-stranded DNA molecule and achieve seamless splicing. The master mix can be purchased from NEB or SGI-DNA, or can be prepared by the technicians themselves (see Miller lab Protocol).

As used herein, the terms "reporter gene" and "marker gene" can be used interchangeably and refer to any marker gene whose expression can be selected or enriched. Specifically, when the marker gene is expressed in cell, the cell expressing the marker gene can be selected and enriched in a certain manner. Reporter genes that can be used in the present invention include, but are not limited to, the fluorescent protein genes that can be sorted by FACS after expression, or resistance genes that can be screened by antibiotics, or protein genes that can be recognized by the corresponding antibody and screened by immunostaining or magnetic bead adsorption after expression. Resistance genes that can be used in the present invention include, but are not limited to, those of blasticidin, geneticin (G-418), hygromycin B, mycophenolic acid, puromycin, zeocin or neomycin. The fluorescent protein genes that can be used in the present invention include, but are not limited to, those of cyan fluorescent protein, green fluorescent protein, enhanced green fluorescent protein, yellow fluorescent protein, orange fluorescent protein, red fluorescent protein, far-red fluorescent protein or switchable fluorescent proteins, preferably enhanced green fluorescent protein (EGFP).

sgRNA

Generally, sgRNA, also known as a "single-stranded guide RNA", which is a RNA strand fused by crRNA and tracrRNA. As known to the technicians of this field, sgRNA contains a sequence paired with a target sequence (also termed as gRNA pairing sequence or sgRNA pairing sequence), a scaffold sequence (also termed as gRNA scaffold sequence or sgRNA scaffold sequence) and transcription terminators (such as polyA). In the present invention, gRNAs and sgRNAs can be used interchangeably unless otherwise specified.

In the present invention, the term "gRNA scaffold sequence" or "sgRNA scaffold sequence" refers to the sequence between the gRNA-and-the-target-genome pairing sequence and the transcription terminator in the sgRNA. Preferably, the sgRNA scaffold sequence is selected from the group consisting of: target site pairing sequence, sgRNA scaffold and transcription termination sequence "TTTTTT", with the specific sequence as shown below: 5'-GTTT-TAGAGCTAGAAATAGCAAGT-TAAAATAAGGCTAGTCCGTTATCAACTTGAA AAAGTGGCACCGAGTCGGTGCTTTTTT (SEQ ID NO.: 165)-3', with the detection Primer-R underlined.

In the present invention, the methods and tools for gRNA (sgRNA) design can be conventional and available in many ways, including but are not limited to: sgRNAcas9, E-CRISP, and/or CHOPCHOP.

Porcine Whole Genome sgRNA Library

The present invention provides a porcine whole genome specific sgRNA library, which includes:

(i) N types of vectors expressing porcine-specific sgRNAs, wherein N is a positive integer ≥20,000. The porcine-specific sgRNA is a target gene for the whole genome, which is selected from (a) protein coding gene, (b) lincRNA, (c) miRNA, (d) a combination of (a), (b) and (c). Furthermore, the porcine-specific sgRNA has the following structural features:

(1) The target gene locus targeted by sgRNA contains PAM as NGG, and preferably, the sgRNA is $N_{20}$NGG (N is any base of A, T, C, and G);

(2) The length of sgRNA is 19 or 20 nt;

(3) The GC content of sgRNA is 40-60%;

(4) the whole-genome off-target evaluation of sgRNA selects off-target sites that do not contain 1 and 2 base mismatches, compared with other sgRNAs, sgRNAs with a relatively small number of off-targets are selected;

(5) for a porcine-specific sgRNA that targets a protein-coding gene, the binding position thereof is located in a region 500 bp downstream of the start codon ATG of the coding gene; for a porcine-specific sgRNA that targets a lincRNA gene, the binding position thereof is located in a 500 bp region downstream of the lincRNA transcription start point; for a porcine-specific sgRNA that targets a miRNA gene, the binding position thereof is a miRNA precursor sequence or a mature sequence; and (ii) optionally, M kinds of negative control vectors, which are the vectors expressing Non-Targeting Control (NTC) sgRNA, wherein M is a positive integer.

Preferably, a whole genome-wide CRISPR/Cas9 knock-out library is designed as follows: The software used is sgRNAcas9 with the version number of "sgRNAcas9_3.0.5". The main technical indicators determine the best parameters based on experimental data, including: PAM on the genome recognized by sgRNA can be chosen from NAG or NGG, preferably NGG; sgRNA length can be selected from 17 nt, 18 nt, 19 nt, and 20 nt, preferably 20 nt; The GC content of sgRNA can be selected in the range of 20%-80%, preferably 40%-60%. The whole genome off-target evaluation of sgRNA examines 5 base mismatches, it is preferred that the sgRNA is the only one that exists on the genome, and does not contain 1 and 2 base mismatch off-target sites and has the minimal all off-target sites. For sgRNA localization, targeting the full-length sequence of the coding gene, that is, the CDS coding region, preferably within the 500 bp region downstream of the start codon ATG; targeting the full-length lincRNA sequence, preferably within the 500 bp region of the transcription initiation; targeting the full-length miRNA sequence, preferably, the miRNA precursor sequence is targeted, and the mature sequence of the miRNA is more preferred. One gene can design 1 to 10 sgRNAs, preferably one gene can design 3 to 5 sgRNAs; the sgRNA library needs to design nonsense sgRNA as a negative control, and the sgRNA used as a negative control has no target on the genome, 100 to 2000 of which can be chosen. It is preferable to design 1000 of which.

Procedures for Construction of Library

This invention provides a method for preparation of the porcine whole genome-specific sgRNA library, comprising the steps of:

(a) Providing a nucleic acid construct Z1, which has the structure of AL-N20-AR, wherein AL is a left homologous arm sequence upstream of the coding sequence of the porcine-specific sgRNA; $N_{20}$, the coding sequence of a porcine-specific sgRNA; AR, a right homologous arm sequence downstream of the coding sequence of the porcine-specific sgRNA (preferably, after the expression sgRNA vector is linearized by a restriction enzyme, the right homologous vector sequence next to downstream of the restriction enzyme restriction site);

(b) using the nucleic acid construct Z1 as a template to perform PCR amplification to obtain an amplification products;

(c) mixing the amplification product with a linearized expression vector and using a Gibson assembly method to ligate, thereby forming a ligation product;

(d) transforming the ligation product into E. coli to obtain a transformant;

(e) extracting a plasmid from the transformant, thereby obtaining the porcine whole genome-specific sgRNA library.

Preferably, the method for constructing a whole genome CRISPR/Cas9 knockout library is as follows:

(1) The alternative vector backbones are common sgRNA expression vectors, such as PX330, PX458, and sgRNA lentiviral expression vectors, such as lenti-sgRNA-EGFP. To ensure that the vast majority of sgRNAs in the sgRNA library can enter the cells, the sgRNA lentivirus expression vector (lenti-sgRNA-EGFP) is preferred, i.e., the cells are infected by the lentivirus to achieve higher integration efficiency. The vector can carry a selection marker gene, such as Neo, Puro, BFP, and EGFP, preferably EGFP, which can facilitate the subsequent sorting of positive infected cells by flow cytometry.

(2) The synthetic oligonucleotide probe pool containing the sgRNA sequence can be ligated into the sgRNA lentivirus expression vector, the alternative methods are:

(A) After flanking the sgRNA sequence with a PCR amplified linker sequence 5'-ACAGGCCCAAGATCGT-GAAGAAGACAGCACCG (SEQ ID NO.: 166) $N_{20}$GTTTCTGTCTTCCAAGAAGCGCAAGGAG (SEQ ID NO.: 167)-3' ($N_{20}$ represents the sgRNA sequence), a high-throughput method is used to synthesize the 85,674-oligonucleotide probe pool, through PCR amplification (the amplification primer sequence is F: 5'-ACAGGCCCAA-GATCGTGAA-3' (SEQ ID NO.: 127), R: 5'-CTCCTTGCGCTTCTTGGA-3' (SEQ ID NO.:128), digestion and ligation to the target vector. Monoclonal colony is selected for Sanger sequencing to identify the ligation efficiency.

(B) The homologous arm are attached to both sides of the sgRNA sequence, homologous arm is the sequence at both ends after digestion and linearization by the target vector: 5'-TATCTTGTGGAAAGGACGAAACACCG (SEQ ID NO.: 163) $N_{20}$GTTTTAGAGCTAGAAATAGCAAGTTAAAAT (SEQ ID NO.: 164)-3' ($N_{20}$ is the sgRNA sequence), a 85,674-oligonucleotide probe pool is synthesized by high-throughput method, followed by PCR amplification (amplification primer sequence is: F: 5'-GGCTTTATATATCTTGTG-GAAAGGACGAAACACCG-3' (SEQ ID NO.:130), R: 5'-CTAGCCTTATTTTAACTTGCTAT-TTCTAGCTCTAAAAC-3' (SEQ ID NO.:131) and Gibson assembly method, it was ligated with the target vector by homologous recombination.

The ligation efficiency was determined first by TA clone sequencing, and finally the sgRNA sequence abundance in the library was identified by high-throughput sequencing. A comparison of the ligation efficiency of the two methods for constructing lentiviral expression sgRNA vector reveals Method B >Method A.

(3) To expand culture and extract the plasmid, the successfully ligated lentivirus expression sgRNA vectors can be introduced into *E. coli* cells by 1) chemical transformation or 2) electrotransformation. In China, it is difficult to obtain high-quality electrocompetent cells from companies like NEB or Thermo, so the chemical transformation method is preferred. The *E. coli* cells used is Transl-T1 Phage Resistant Chemically Competent Cell (TransGen), followed by the Gibson assembly strategy and higher transformation efficiency can be achieved and a recombinant vector library of sgRNAs with a coverage of 200× of transformants can be obtained.

(4) After transformation, the cloned strain on the LB plate can be expanded and cultured by scraping into the liquid culture medium, or directly inoculated into the liquid culture medium after transformation to expand the culture. After incubation on a 37° C. shaker for 12-16 hours, the bacteria are collected to extract the plasmid. As chemical transforamation is less efficient than electrotransformation, it requires a large number of bacterial transformation reactions, and the method of scraping clones by spreading a plate i is a huge workload, so the direct inoculation method after transformation is preferred.

(5) The coverage and abundance of sgRNAs in the CRISPR/Cas9 plasmid library are identified by PCR amplification, library construction, and high-throughput sequencing. For the optimal detection effect, the preferred combination of primer pair is lenti-F1/R6 (121 bp) or lenti-F3/R6 (153 bp) as follows:

(1)

SEQ ID NO.: 132
lenti-F1: 5'-CTTGTGGAAAGGACGAAACACC-3',,

SEQ ID NO.: 140
lenti-R6: 5'-AAGCACCGACTCGGTGCCA-3',;

(2)

SEQ ID NO.: 134
lenti-F3: 5'-GAAAGTATTTCGATTTCTTGGC-3',,

SEQ ID NO.: 140
lenti-R6: 5'-AAGCACCGACTCGGTGCCA-3',.

(6) Lentiviral packaging and infection ability of the CRISPR/Cas9 plasmid library are tested by using the endotoxin-free plasmid extraction kit to extract the sgRNA mixed pool plasmid, followed by packing the lentivirus in HEK293T cells, collection of virus stock, centrifugation and concentration and titer determination. HEK293T and PK-15 cells are infected with a certain amount of virus solution, and the intensity of GFP brightness can be used to determine whether the lentivirus library can be used. Due to lower efficiency of lentivirus packaging with mixed plasmids than that of a single plasmid, it needs large numbers of lentiviral sgRNA plasmids to transfect HEK293T cells to achieve a higher virus titer.

(7) The sgRNA lentiviral library was infected into a PK-15 cell line stably expressing Cas9, and monoclonal cells expressing GFP were picked, followed by sequencing to determine whether the sgRNA is stably integrated into the cell and whether the genes corresponding to sgRNA are edited.

Kit

This invention provides a kit, which includes:

(a) A first container and the porcine whole genome-specific sgRNA library expression vector of the present invention located in the container; and (b) Instructions describing the instructions for using the porcine whole genome-specific sgRNA library.

Preferably, the kit also includes:

(c) A second container and a porcine cell located in the second container, the porcine cell contains a constitutive or inducible Cas9 protein expression vector.

Preferably, the porcine cell is selected from the group consisting of: Porcine PK-15 cells, 3D4/21 cells, and a combination thereof.

Preferably, the porcine cell is a PK-15 cell line capable of stably expressing Cas9, and genome knockout efficiency can be improved by using this cell line in combination with the porcine whole genome CRISPR/Cas9 knockout library plasmid kit for high-throughput screening of porcine functional genes.

Preferably, the present invention provides a porcine whole genome CRISPR/Cas9 knockout library plasmid kit. The kit contains a lentiviral vector expressing Cas9, a porcine whole-genome sgRNA lentiviral plasmid designed and constructed by the method of the present invention, a total of 82,392 sgRNAs are obtained through high-throughput sequencing, which can target 14,958 porcine coding genes, 14,168 lincRNAs and 142 miRNAs respectively, and it also contains 970 negative control sgRNAs.

The main advantages of the present invention include:

(1) This invention discloses for the first time a method for designing and constructing a whole-genome CRISPR/Cas9 knockout library, with the features of a short sgRNA cycle for the design at the whole genome-wide level, high accuracy of synthetic sgRNA oligonucleotide sequences, and high ligation efficiency of sgRNA recombination vectors during library construction.

(2) The present invention discloses for the first time a porcine whole genome-wide CRISPR/Cas9 knockout library plasmid kit, with a high specificity of sgRNAs contained in the kit, and the target sites cover the porcine whole genome-wide coding or non-coding genes, which is very suitable for high-throughput screening of porcine functional genes.

(3) The present invention also provides a PK-15 cell line stably expressing Cas9, the use of which can reduce the transfection of an exogenous Cas9 expression vector and improve genome editing efficiency.

The present invention is further demonstrated by the following specific embodiments. It should be noted that these examples are only used to illustrate the present invention rather than limit its scope. The experimental methods without detailed conditions in the following examples are generally performed according to the conventional conditions as described in Molecular Cloning: Laboratory Manual by Sambrook et al. (New York: Cold Spring Harbor Laboratory Press, 1989), or according to the manufacturer's instructions. Unless otherwise stated, percentages and parts are estimated by weight.

Unless otherwise specified, the materials used in the examples are all available in China.

Example 1

Figure 2:
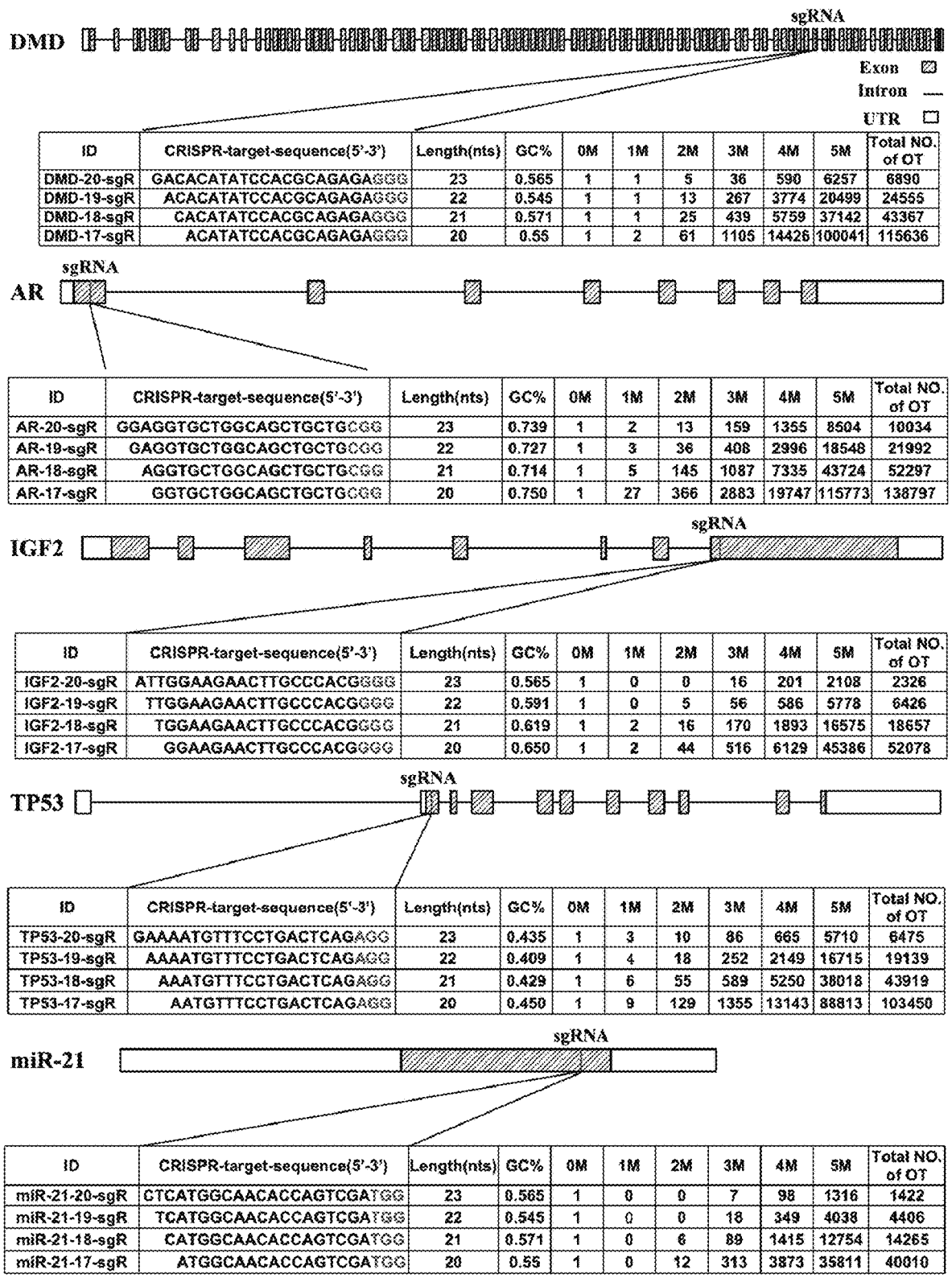
FIG. 2 is a comparative analysis of the number of off-target sites of sgRNAs with a different length targeting the same site for seven protein coding genes and two miRNAs in Example 1 of the present invention. Wherein 0M indicates sgRNA targeting site, and 1M-5M indicates the sgRNA off-target sites. Among them, 1M indicates an off-target site with abase mismatch; 2M, an off-target site with two base mismatches; 3M, an off-target site with three base mismatches; 4M, an off-target site with four base mismatches; 5M, an off-target site with five base mismatches; and Total NO. of OT, the total number of off-target sites.
Figure 2:
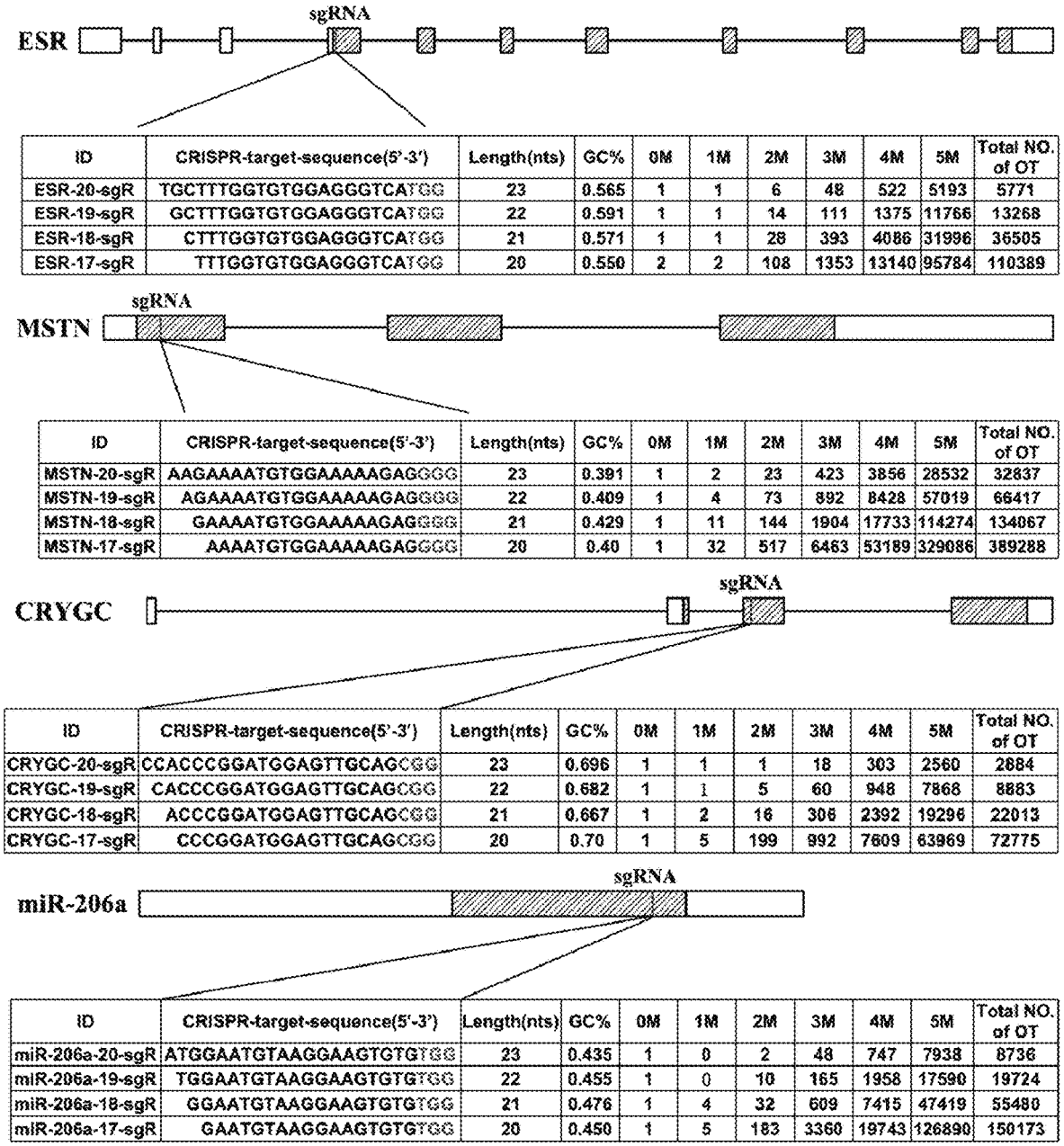
Figure 3:
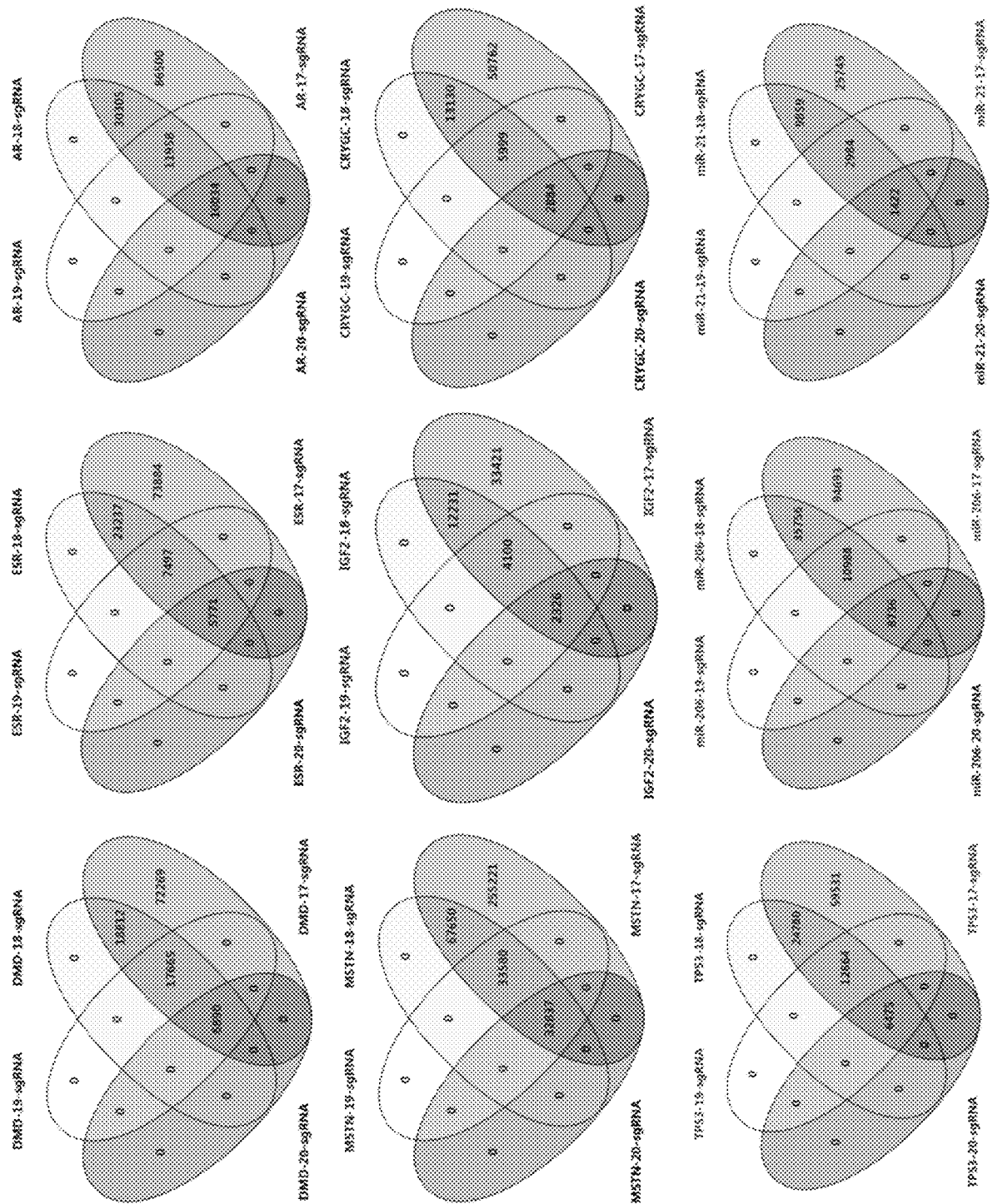
FIG. 3. Venn diagram analysis of off-target sites of different-length sgRNAs targeting the same site for seven protein coding genes and two miRNAs in Example 1 of the present invention.

Determining Optimal Parameters for the Whole Genome CRISPR/Cas9 Knockout Library Design A whole genome CRISPR/Cas9 knockout library can be used for high-throughput screening of functional genes. However, the CRISPR/Cas9 system has off-target effects, secondly, the activity or off-target effects of sgRNAs with a different length may be different. To determine the optimal parameters for whole genome CRISPR/Cas9 knockout library design, sgRNAcas9 software is used to design sgRNAs and evaluate the off-target effects for 100 genes randomly selected from the human genome, compare the off-target effects of sgRNAs with lengths of 17, 18, 19, and 20 nt and verify their activity and the law of specificity of four different lengths of sgRNA using the experiments. As shown in FIG. 1A, PAM is selected as NGG, and the specificity evaluation of sgRNAs or classification of off-target effects is Discard: there is no corresponding target binding site in the genome; High_risk: there is an off-target site with 1 base mismatch, in which the seed sequence contained is completely matched, and the non-seed sequence contains only one base-mismatched off-target site; Moderate_risk: there are 2 base mismatched off-target sites, in which the seed sequence contained is completely matched, and the non-seed sequence contains no more than 2 base mismatched off-target sites; Low_risk: there are more than 2 base mismatched off-target sites; Repeat_sites_or_bad: there are multiple perfectly matched target binding sites; Best: there are no off-target sites with less than 2 base mismatches and it does not contain off-target binding sites that completely match the seed sequence. In FIG. 1B, it is shown that as the length of the sgRNA decreases, the number of the best sgRNAs is getting smaller and smaller, coupled with an increase in the number of the high risk sgRNAs. In FIG. 1C, it is also shown that with a decrease of sgRNA length, the number of predicted off-target sites containing 1 or 2 base mismatches increases, which may increase the risk of off-target. Additionally, we randomly selected sgRNAs targeting 7 genes and 2 miRNAs at the same site but with different lengths for off-target analysis. In FIG. 2, the number of off-target sites predicted by sgRNAs was shown to increase significantly with the decrease of sgRNA length. Wayne diagram analysis reveals that sgRNA with a length of 17 nt predicted the largest number of off-target sites, including those shared by 18, 19 and 20 nt (FIG. 3).

Furthermore, we verified the activity and off-target effects of different-length sgRNAs on HEK293T cells. The sgRNA sequence and primer sequence of the target gene are shown below:

The sequence of sgRNA is:

| sgRNA | Sequence (5'-3') | SEQ ID NO.: |
|---|---|---|
| DMD-20-sgRNA | GACACATATCCACGCAGAGAGGG | 1 |
| DMD-19-sgRNA | ACACATATCCACGCAGAGAGGG | 2 |
| DMD-18-sgRNA | CACATATCCACGCAGAGAGGG | 3 |
| DMD-17-sgRNA | ACATATCCACGCAGAGAGGG | 4 |
| ESR-20-sgRNA | TGCTTTGGTGTGGAGGGTCATGG | 5 |
| ESR-19-sgRNA | GCTTTGGTGTGGAGGGTCATGG | 6 |
| ESR-18-sgRNA | CTTTGGTGTGGAGGGTCATGG | 7 |
| ESR-17-sgRNA | TTTGGTGTGGAGGGTCATGG | 8 |
| Mir-21-20-sgRNA | CTCATGGCAACACCAGTCGATGG | 9 |
| Mir-21-19-sgRNA | TCATGGCAACACCAGTCGATGG | 10 |
| Mir-21-18-sgRNA | CATGGCAACACCAGTCGATGG | 11 |
| Mir-21-17-sgRNA | ATGGCAACACCAGTCGATGG | 12 |
| AR-20-sgRNA | GGAGGTGCTGGCAGCTGCTGCGG | 13 |
| AR-19-sgRNA | GAGGTGCTGGCAGCTGCTGCGG | 14 |
| AR-18-sgRNA | AGGTGCTGGCAGCTGCTGCGG | 15 |
| AR-17-sgRNA | GGTGCTGGCAGCTGCTGCGG | 16 |
| TP53-20-sgRNA | GAAAATGTTTCCTGACTCAGAGG | 17 |
| TP53-19-sgRNA | AAAATGTTTCCTGACTCAGAGG | 18 |
| TP53-18-sgRNA | AAATGTTTCCTGACTCAGAGG | 19 |
| TP53-17-sgRNA | AATGTTTCCTGACTCAGAGG | 20 |
| CRYGC-20-sgRNA | CCACCCGGATGGAGTTGCAGCGG | 21 |
| CRYGC-19-sgRNA | CACCCGGATGGAGTTGCAGCGG | 22 |

| sgRNA | Sequence (5'-3') | SEQ ID NO.: |
|---|---|---|
| CRYGC-18-sgRNA | ACCCGGATGGAGTTGCAGCGG | 23 |
| CRYGC-17-sgRNA | CCCGGATGGAGTTGCAGCGG | 24 |
| MSTN-20-sgRNA | AAGAAAATGTGGAAAAAGAGGGG | 25 |
| MSTN-19-sgRNA | AGAAAATGTGGAAAAAGAGGGG | 26 |
| MSTN-18-sgRNA | GAAAATGTGGAAAAAGAGGGG | 27 |
| MSTN-17-sgRNA | AAAATGTGGAAAAAGAGGGG | 28 |
| MIR-206a-20-sgRNA | ATGGAATGTAAGGAAGTGTGTGG | 29 |
| MIR-206a-19-sgRNA | TGGAATGTAAGGAAGTGTGTGG | 30 |
| MIR-206a-18-sgRNA | GGAATGTAAGGAAGTGTGTGG | 31 |
| MIR-206a-17-sgRNA | GAATGTAAGGAAGTGTGTGG | 32 |
| IGF2-20-sgRNA | ATTGGAAGAACTTGCCCACGGGG | 33 |
| IGF2-19-sgRNA | TTGGAAGAACTTGCCCACGGGG | 34 |
| IGF2-18-sgRNA | TGGAAGAACTTGCCCACGGGG | 35 |
| IGF2-17-sgRNA | GGAAGAACTTGCCCACGGGG | 36 |

Primers Used to Construct the sgRNA Expression Vectors are:

| Primer | Sequence (5'-3') | SEQ ID NO.: |
|---|---|---|
| DMD-20-sgRNA-F | caccGACACATATCCACGCAGAGA | 37 |
| DMD-20-sgRNA-R | aaacTCTCTGCGTGGATATGTGTC | 38 |
| DMD-19-sgRNA-F | caccACACATATCCACGCAGAGA | 39 |
| DMD-19-sgRNA-R | aaacTCTCTGCGTGGATATGTGT | 40 |
| DMD-18-sgRNA-F | caccCACATATCCACGCAGAGA | 41 |
| DMD-18-sgRNA-R | aaacTCTCTGCGTGGATATGTG | 42 |
| DMD-17-sgRNA-F | caccACATATCCACGCAGAGA | 43 |
| DMD-17-sgRNA-R | aaacTCTCTGCGTGGATATGT | 44 |
| ESR-20-sgRNA-F | caccTGCTTTGGTGTGGAGGGTCA | 45 |
| ESR-20-sgRNA-R | aaacTGACCCTCCACACCAAAGCA | 46 |
| ESR-19-sgRNA-F | caccGCTTTGGTGTGGAGGGTCA | 47 |
| ESR-19-sgRNA-R | aaacTGACCCTCCACACCAAAGC | 48 |
| ESR-18-sgRNA-F | caccCTTTGGTGTGGAGGGTCA | 49 |
| ESR-18-sgRNA-R | aaacTGACCCTCCACACCAAAG | 50 |
| ESR-17-sgRNA-F | caccTTTGGTGTGGAGGGTCA | 51 |
| ESR-17-sgRNA-R | aaacTGACCCTCCACACCAAA | 52 |
| Mir-21-20-sgRNA-F | caccCTCATGGCAACACCAGTCGA | 53 |
| Mir-21-20-sgRNA-R | aaacTCGACTGGTGTTGCCATGAG | 54 |
| Mir-21-19-sgRNA-F | caccTCATGGCAACACCAGTCGA | 55 |
| Mir-21-19-sgRNA-R | aaacTCGACTGGTGTTGCCATGA | 56 |
| Mir-21-18-sgRNA-F | caccCATGGCAACACCAGTCGA | 57 |
| Mir-21-18-sgRNA-R | aaacTCGACTGGTGTTGCCATG | 58 |
| Mir-21-17-sgRNA-F | caccATGGCAACACCAGTCGA | 59 |
| Mir-21-17-sgRNA-R | aaacTCGACTGGTGTTGCCAT | 60 |
| AR-20-sgRNA-F | caccGGAGGTGCTGGCAGCTGCTG | 61 |
| AR-20-sgRNA-R | aaacCAGCAGCTGCCAGCACCTCC | 62 |
| AR-19-sgRNA-F | caccGAGGTGCTGGCAGCTGCTG | 63 |
| AR-19-sgRNA-R | aaacCAGCAGCTGCCAGCACCTC | 64 |
| AR-18-sgRNA-F | caccAGGTGCTGGCAGCTGCTG | 65 |
| AR-18-sgRNA-R | aaacCAGCAGCTGCCAGCACCT | 66 |
| AR-17-sgRNA-F | caccGGTGCTGGCAGCTGCTG | 67 |
| AR-17-sgRNA-R | aaacCAGCAGCTGCCAGCACC | 68 |
| TP53-20-sgRNA-F | caccGAAAATGTTTCCTGACTCAG | 69 |
| TP53-20-sgRNA-R | aaacCTGAGTCAGGAAACATTTTC | 70 |
| TP53-19-sgRNA-F | caccAAAATGTTTCCTGACTCAG | 71 |
| TP53-19-sgRNA-R | aaacCTGAGTCAGGAAACATTTT | 72 |
| TP53-18-sgRNA-F | caccAAATGTTTCCTGACTCAG | 73 |
| TP53-18-sgRNA-R | aaacCTGAGTCAGGAAACATTT | 74 |
| TP53-17-sgRNA-F | caccAATGTTTCCTGACTCAG | 75 |
| TP53-17-sgRNA-R | aaacCTGAGTCAGGAAACATT | 76 |
| CRYGC-20-sgRNA-F | caccCCACCCGGATGGAGTTGCAG | 77 |
| CRYGC-20-sgRNA-R | aaacCTGCAACTCCATCCGGGTGG | 78 |
| CRYGC-19-sgRNA-F | caccCACCCGGATGGAGTTGCAG | 79 |
| CRYGC-19-sgRNA-R | aaacCTGCAACTCCATCCGGGTG | 80 |
| CRYGC-18-sgRNA-F | caccACCCGGATGGAGTTGCAG | 81 |
| CRYGC-18-sgRNA-R | aaacCTGCAACTCCATCCGGGT | 82 |
| CRYGC-17-sgRNA-F | caccCCCGGATGGAGTTGCAG | 83 |
| CRYGC-17-sgRNA-R | aaacCTGCAACTCCATCCGGG | 84 |
| MSTN-20-sgRNA-F | caccAAGAAAATGTGGAAAAAGAG | 85 |
| MSTN-20-sgRNA-R | aaacCTCTTTTTCCACATTTTCTT | 86 |
| MSTN-19-sgRNA-F | caccAGAAAATGTGGAAAAAGAG | 87 |
| MSTN-19-sgRNA-R | aaacCTCTTTTTCCACATTTTCT | 88 |
| MSTN-18-sgRNA-F | caccGAAAATGTGGAAAAAGAG | 89 |
| MSTN-18-sgRNA-R | aaacCTCTTTTTCCACATTTTC | 90 |
| MSTN-17-sgRNA-F | caccAAAATGTGGAAAAAGAG | 91 |
| MSTN-17-sgRNA-R | aaacCTCTTTTTCCACATTTT | 92 |
| MIR-206a-20-sgRNA-F | caccATGGAATGTAAGGAAGTGTG | 93 |
| MIR-206a-20-sgRNA-R | aaacCACACTTCCTTACATTCCAT | 94 |

| Primer | Sequence (5'-3') | SEQ ID NO.: |
|---|---|---|
| MIR-206a-19-sgRNA-F | caccTGGAATGTAAGGAAGTGTG | 95 |
| MIR-206a-19-sgRNA-R | aaacCACACTTCCTTACATTCCA | 96 |
| MIR-206a-18-sgRNA-F | caccGGAATGTAAGGAAGTGTG | 97 |
| MIR-206a-18-sgRNA-R | aaacCACACTTCCTTACATTCC | 98 |
| MIR-206a-17-sgRNA-F | caccGAATGTAAGGAAGTGTG | 99 |
| MIR-206a-17-sgRNA-R | aaacCACACTTCCTTACATTC | 100 |
| IGF2-20-sgRNA-F | caccATTGGAAGAACTTGCCCACG | 101 |
| IGF2-20-sgRNA-R | aaacCGTGGGCAAGTTCTTCCAAT | 102 |
| IGF2-20-sgRNA-F | caccTTGGAAGAACTTGCCCACG | 103 |
| IGF2-20-sgRNA-R | aaacCGTGGGCAAGTTCTTCCAA | 104 |
| IGF2-20-sgRNA-F | caccTGGAAGAACTTGCCCACG | 105 |
| IGF2-20-sgRNA-R | aaacCGTGGGCAAGTTCTTCCA | 106 |
| IGF2-20-sgRNA-F | caccGGAAGAACTTGCCCACG | 107 |
| IGF2-20-sgRNA-R | aaacCGTGGGCAAGTTCTTCC | 108 |

The designed primers were sent to the company for synthesis and ligated to the BbsI-digested PX330 vector (full name of pX330-U6-Chimeric_BB-CBh-hSpCas9, addgene, 42230) after annealing. The sgRNA primer annealing system (10 μL): sgRNA-F: 5 μL and sgRNA-R: 5 μL; annealing procedure: 95° C., 10 min; 65° C., 1 h. The annealing product is ligated into the digested pX330 vector through the BbsI digestion site. After successful identification by sequencing, the plasmid is extracted using an endotoxin-free plasmid extraction kit (OMEGA, D6950-01), followed by determining the plasmid concentration with a Nandrop 2000 concentration meter, and then transfecting it to HEK293T cells at a confluency of about 80%, cells were transfected according to the instructions of the transfection reagent Lipofectamine 2000 (Thermo, #11668027).

We compared the cleavage activity of different-length sgRNAs targeting 7 genes and 2 miRNAs at the same site. At 48 hours post transfection, cells were collected and DNA was extracted according to the instructions of Tiangen DNA Extraction Kit (TIANGEN, DP304-03). PCR amplification was performed using the following PCR amplification primers:

| DMD-F | TCACCCAATGCCAGTGAGAT | SEQ ID NO.: 109 |
|---|---|---|
| DMD-R | TATCTCCAGGAGCACAGCCA | SEQ ID NO.: 110 |
| ESR-F | CTGGATCCGTCTTTCGCGTT | SEQ ID NO.: 111 |
| ESR-R | GCTCGTTCTCCAGGTAGTAGG | SEQ ID NO.: 112 |
| Mir-21-F | TGAAACTGGGCTGCTGCATA | SEQ ID NO.: 113 |
| Mir-21-R | AACCACGACTAGAGGCTGAC | SEQ ID NO.: 114 |
| AR-F | GCCGTCCAAGACCTACCGA | SEQ ID NO.: 115 |
| AR-R | ATGCTCCAACGCCTCCACA | SEQ ID NO.: 116 |
| TP53-F | AAGGGAGTTGGGAATAGGGTG | SEQ ID NO.: 117 |
| TP53-R | AGGGGGACTGTAGATGGGTGA | SEQ ID NO.: 118 |
| CRYGC-F | GGCATTCTACCTCAGCAACC | SEQ ID NO.: 119 |
| CRYGC-R | AACCTCCCTCCCTGTAACC | SEQ ID NO.: 120 |
| MSTN-F | AGATTCACTGGTGTGGCAAG | SEQ ID NO.: 121 |
| MSTN-R | GATTGTTTCCGTTGTAGCGTG | SEQ ID NO.: 122 |
| Mir-206a-F | GAGTGGCTCTCTGCGTGAAT | SEQ ID NO.: 123 |
| Mir-206a-R | GCTTCCTTGGTGAGGGAGTC | SEQ ID NO.: 124 |
| IGF2-F | TAACACGGCTCTCTCTGTGC | SEQ ID NO.: 125 |
| IGF2-R | GAGTAGCCTGTTTCGGGGAG | SEQ ID NO.: 126 |

The PCR reaction system: 10×LA PCR buffer: 5 μL; dNTP mixture ($Mg^2$+plus): 4 μL; forward primer: 1 μL; reverse primer: 1 μL; DNA: (20-50) ng; and water was added to 50 μL. The PCR reaction program: 95° C., 10 min; 32 cycles (95° C., 30 s; 60° C., 30 s; 72° C., 1 min); 72° C., 5 min; 15° C., 2 min. PCR product was purified according to the instructions of the TAKARA purification kit (Takara, 9701) after PCR was completed, and the annealing reaction was performed on a PCR instrument. The total annealing reaction volume (19.5 μL): 10×NEBuffer2: 2 μL; DNA: 200 ng; and water was added to 19.5 μL. The annealing procedure: 95° C., 5 min; 95-85° C., −2° C./s; 85-25° C., −0.1° C./s; 4° C., 2 min. After annealing, T7EN1 (NEB, M0302) was used for digestion, the enzyme digestion system: annealed PCR product: 19.5 μL; T7 Endonuclease I: 0.5 μL; digestion with water bath at 37° C. for 15 min, it was detected by 2% common agarose gel electrophoresis.

Figure 4:
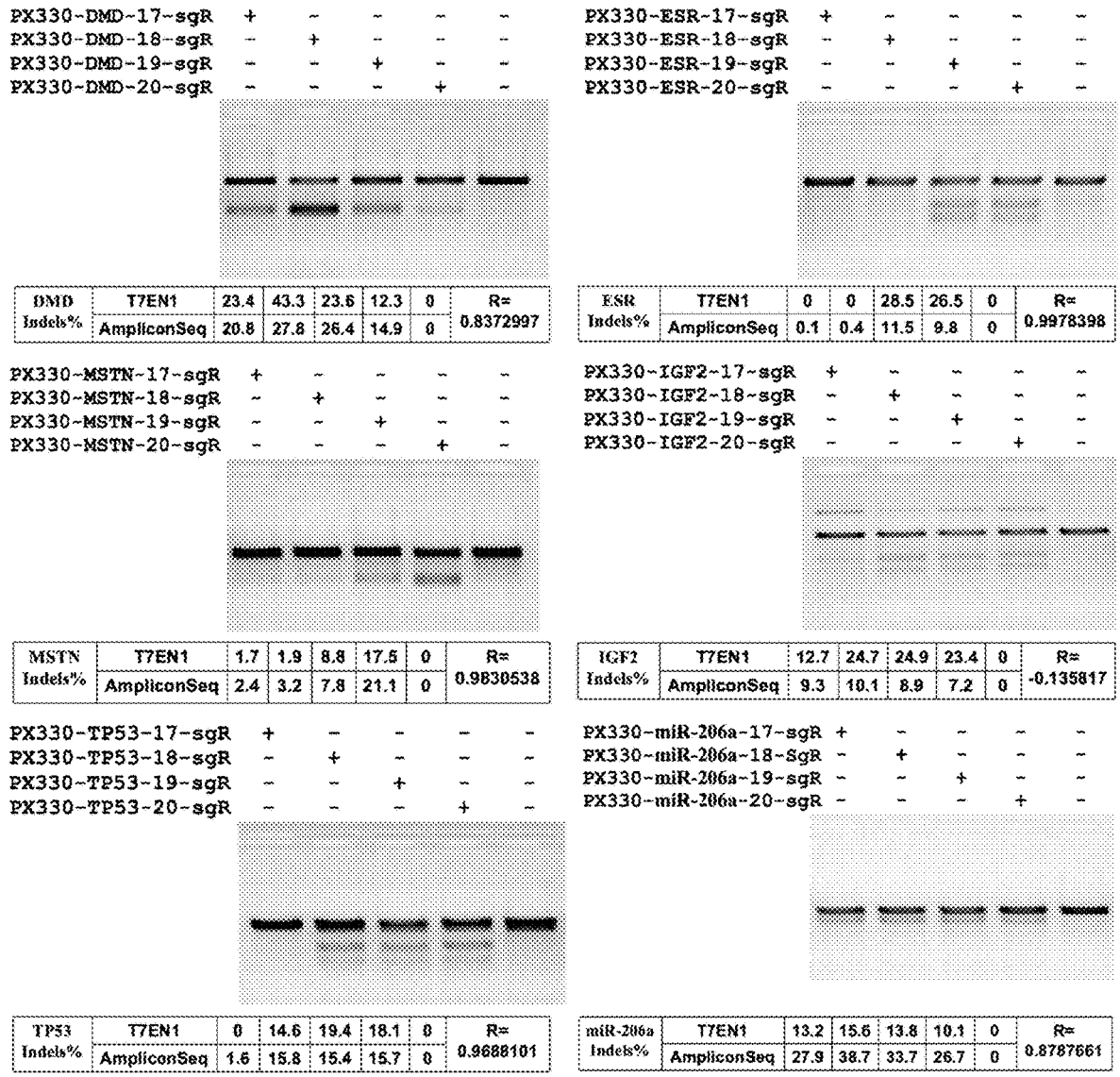
FIG. 4. T7EN1 enzyme digestion identification of different-length sgRNAs targeting the same site for 7 protein-coding genes and 2 miRNAsassay in Example 1 of the present invention.
Figure 4:
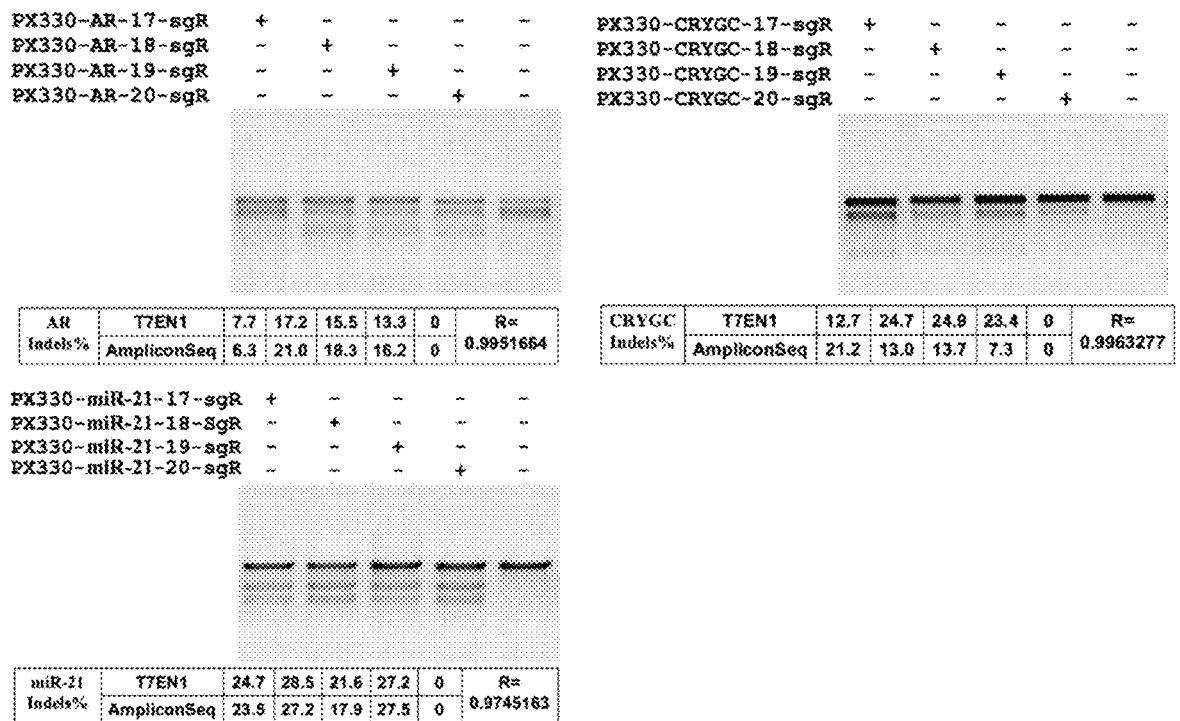

As shown in FIG. 4, the activity of sgRNAs with different lengths is related to the target. For example, when targeting the DMD gene, the 18 nt sgRNA has the highest cleavage activity, in contrast to no activity for 17 nt and 18 nt of sgRNAs targeting the ESR gene and comparable activity for sgRNAs with different lengths targeting miR-21.

Meanwhile, off-target verification was performed for different-length sgRNAs targeting the AR genes by randomly selecting 19 sites. Specifically, the PCR products were directly sequenced and digested with T7EN1, and the efficiency was evaluated by the TIDE software through the PCR sequencing results. In FIGS. 5 A and B, the off-target sites of sgRNAs with different lengths contain 1-5 mismatched bases, all with genomic cleavage, and sites with a cleavage efficiency greater than 6% are set to have off-target activity. The number of off-target sites that can be verified with different lengths is comparable, indicating the existence of off-target effects in sgRNAs of different lengths, but the predicted number of off-targets shows the number of off-targets predicted by short sgRNAs increased significantly. Therefore, the 20 nt sgRNA is preferred.

Based on the above experimental data and published literature reports, the optimal parameters for designing the whole genome CRISPR/Cas9 knockout library with high specificity are determined as follows:

(1) NGG as the PAM of the sgRNA (preferably, sgRNA is $N_{20}$NGG (N is any base of A, T, C, G);
(2) The sgRNA with a length of 19 or 20 nt;
(3) The GC content of sgRNA from 40-60%;
(4) the whole-genome off-target evaluation of sgRNA selects off-target sites that do not contain 1 and 2 base mismatches, compared with other sgRNAs, sgRNAs with a relatively small number of off-targets are selected;

(5) For sgRNA localization, the 500 bp region downstream of the start codon ATG is selected when targeting the coding gene; the region within the first 500 bp region of the transcription initiation is selected when targeting the full-length lincRNA sequence; the targeted miRNA precursor or mature sequences are selected when targeting the full-length miRNA sequence.

(6) 3 sgRNAs for each gene;

(7) the negative control required for the sgNRA library, that is the nonsense sgRNA, 1000 pieces are selected.

Example 2

Design of a porcine whole genome CRISPR/Cas9 knockout library All porcine protein coding genes, miRNAs and lincRNAs were used as research objects and the whole genome CRISPR/Cas9 knockout library was designed according to the optimal parameters determined in Strategy 1. The protein coding genes and genomic sequences were downloaded from the Ensembl database. Porcine miRNA sequences were downloaded from the miRBase database. The sequences of lincRNAs were downloaded from the ALDB database. The target gene locus targeted by sgRNA contains PAM as NGG, with a sgRNA length of 20 nt, a GC content of 40-60%, 5 base mismatches by the whole genome off-target assessment of sgRNAs, preferably only present in the genome, an sgRNA that does not contain 1 and 2 base mismatch off-target sites and has a minimum of all off-target sites. Three sgRNAs were designed for each gene, and 1,000 sgRNAs without targets on the genome were designed as negative controls. A total of 85,674 sgRNAs were designed, targeting 17,743 protein-coding genes, 11,053 lincRNAs, and 551 miRNAs respectively.

Based on the designed sgRNAs for the porcine genome, a nucleic acid construct of formula III or IV was prepared by artificial synthesis: 5'-ACAGGCCCAAGATCGT-GAAGAAGACAGCACCG (SEQ ID NO.: 166) N$_{20}$GTTTCTGTCTTCTCCAAGAAGCGCAAGGAG (SEQ ID NO. 167)-3' (III) 5'-TATCTTGTG-GAAAGGACGAAACACCG (SEQ ID NO.: 163) N$_{20}$GTTTTAGAGCTAGAAATAGCAAGTTAAAAT (SEQ ID NO.: 164)-3' (IV) In the formula, N$_{20}$ is the sgRNA sequence.

Example 3

Figure 6:
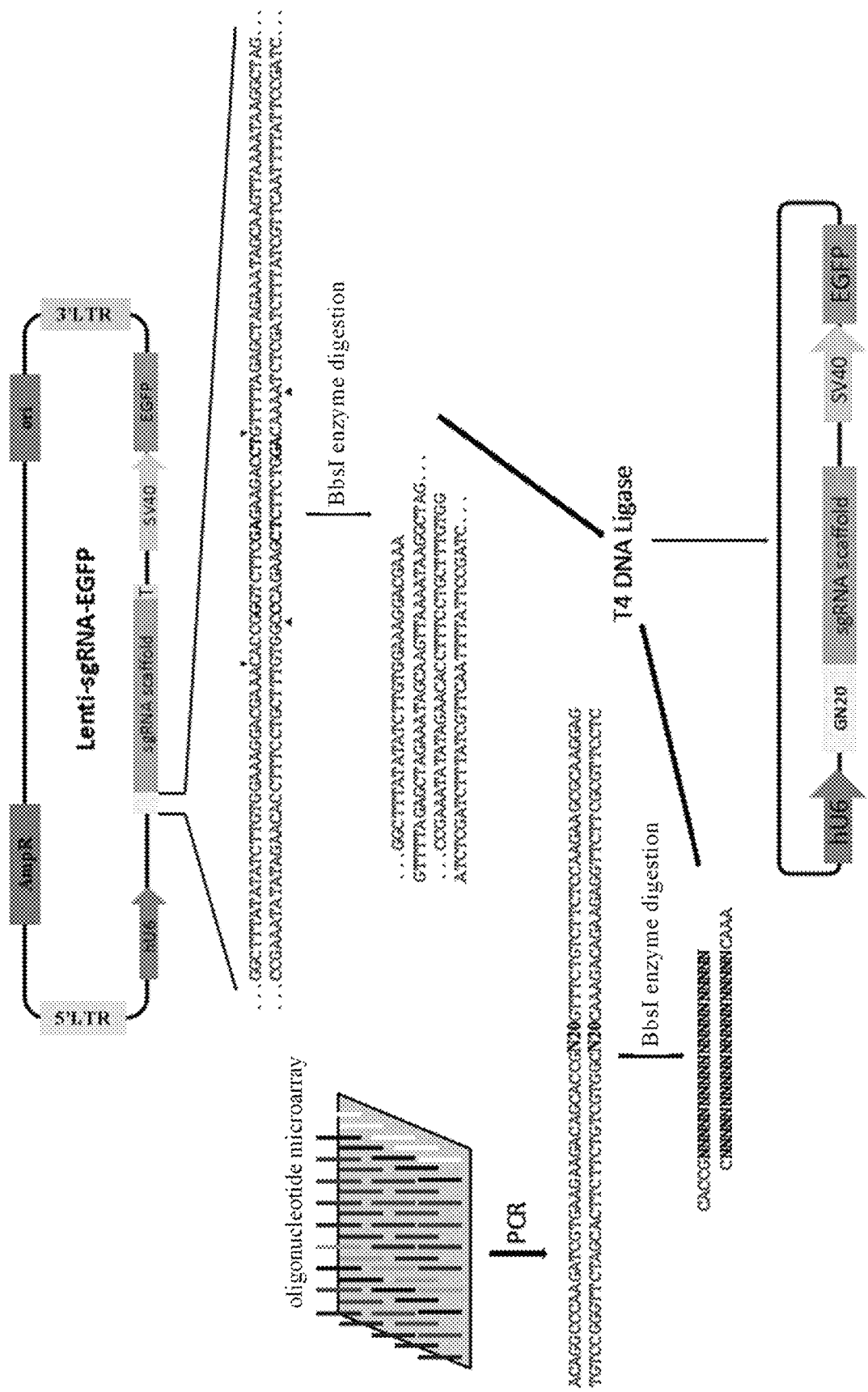
FIG. 6. The schematic diagram of an experiment of the T4 DNA ligase method according to the scheme (1) in Example 3 of the present invention.

Comparison of the Efficiency of Two Different Strategies for Construction of Porcine sgRNA Libraries
Strategy (1): T4 DNA Ligase Method The sgRNA sequence is flanked on both sides by a PCR-amplified adaptor sequence, including a BbsI digestion site, and the designed adaptor sequence is as follows: 5'-ACAGGCCCAAGATCGTGAAGAAGACAGCACCG (SEQ ID NO.: 166) N$_{20}$GTTTCTGTCTTCTCCAAGAAGCGCAAGGAG (SEQ ID NO.: 167)-3' (N$_{20}$ is the sgRNA sequence). The PCR product size is 82 bp, and the library construction process by the T4 DNA ligase method is shown in FIG. 6.

BbsI N20
5-ACAGGCCCAAGATCGTGAAGA-GACAGCACCG (SEQ ID NO.: 166) NNNNNNNNNNNNNNNNNNNNGTTTCTGTCTTCTC-CAAGAAGCGCAAGGAG (SEQ ID NO.: 167)-3-TGTCCGGGTTCTAGCACTTCTTCTGTCGTGGC (SEQ ID NO.: 168) NNNNNNNNNNNNNNNNNNNN-CAAAGACAGAAGAGGTTCTTCGCGTTCCTC(SEQ ID NO.: 169)-5

BbsI
An Example for Probe Design:
>ENSSSSCG00000000001_5_596292_596321_p,
5'-ACAGGCCCAAGATCGTGAAGAA-GACAGCACCGCACGACGTAGTAGAAGCGCAGT TTCTGTCTTCTCCAAGAAGCGCAAGGAG (SEQ ID NO.: 170)-3' (the sgRNA sequence is underlined).

An 82-mer sequence was sent to CustomArray Inc (USA) for synthesis of the 85,674-oligonucleotide pool, followed by library construction of the synthetic oligonucleotide pool and high-throughput sequencing identification. FIG. 7 shows the results with an accuracy of 99.23%.

Next, the oligonucleotide pool was used as a template for PCR amplification with the following amplification primer sequence: Forward primer F: 5'-ACAGGCCCAAGATCGT-GAA-3' (SEQ ID NO.: 127) Reverse primer R: 5'-CTCCTTGCGCTTCTTGGA-3' (SEQ ID NO.: 128) The PCR reaction system: 2×Phusion High-Fidelity PCR Master Mix with HF Buffer: 25 µL; sgRNA library: 1 µL; forward primer: 2 µL; reverse primer: 2 µL; sterile water: 20 µL; reaction procedure: 98° C., 2 min; 8, 10, 12, or 16 cycles were set separately (98° C., 10 s; 60° C., 15 s; 72° C., 45 s); 72° C., 5 min; 15° C., 2 min.

PCR products were subjected to 4% agarose gel electrophoresis and the position of the target band was observed through instrument for gluing, the target band (82 bp) was cut and recovered according to the instructions of QIAGEN Gel Extraction Kit (QIAGEN, 28704), followed by elution with 10 µL. Next, the purified PCR product was digested with BbsI restriction enzyme, enzymatic digestion reaction system: 10×Fast digest buffer: 3 µL; recovered PCR product: 400 ng; BbsI: 2 µL; sterilized water was added to 30 µL. The lenti-sgRNA-EGFP vector was digested, enzymatic digestion reaction system: 10×Fastdigest buffer: 2 µL; Lenti-sgRNA-GFP: 3 µg; BbsI: 3 µL; add sterilized water was added to 20 µL; digestion in a 37° C. water bath for more than 3 hours. Next, the digested product was subjected to 20% acrylamide gel electrophoresis. Use 0.5×TBE for the electrophoresis solution and RNA loading buffer for the loading buffer. Adjust the voltage to 100 v and perform the electrophoresis on ice. The 20% acrylamide gel was prepared: (29% acrylamide and 1% N, N'-methylenebisacrylamide) 29:1: 13.32 mL; sterilized water: 2.54 mL; 5×TBE: 4 mL; 10% ammonium persulfate (AP): 0.14 mL; TEMED: 5 µL).

Recovering DNA fragments from PAGE gels:

(1) When the gel is not completely dry, cut out the target DNA band with a clean surgical blade and place it in a 1.5 mL clean centrifuge tube, followed by washing with 500 µL double distilled water, centrifugation and discarding the double distilled water;

(2) Add 500 µL double distilled water and crush the gel with the sharp of a pipette tip, followed by a 37° C. water bath for 12 h;

(3) After centrifugation at 12,000 rpm for 5 min, transfer the supernatant (DNA crude recovery solution) to another new and clean 1.5 mL centrifuge tube;

(4) Add 2 times the volume of pre-cooled anhydrous ethanol and 1/10 volume of 3 M sodium acetate (pH=5.2) to the supernatant (DNA crude recovery solution), followed by storage at −20° C. for 1 h in a refrigerator;

(5) After centrifugation at 12,000 rpm for 20 min at 4° C., discard the supernatant;

(6) After wash the pellet twice with 75% ethanol, centrifuge the pellet at 4° C. and 1,200 rpm for 2 min and discard the supernatant;

(7) After ethanol has evaporated, dissolve the precipitate in double distilled water;

(8) Detect the concentration of the recovered product by NanoDrop 2000, followed by ligation according to the instructions of ligase (Takara, 6023).

This strategy is used to detect the ligation transformation using 1 ng, 5 ng, 10 ng, and 50 ng purified PCR products, and the total number of clones was counted. As shown in FIG. 8, the number of growing clones is $0.37 \times 10^3$ to $3 \times 10^3$. Additionally, 50 monoclonal colonies were randomly selected for further expanding cultivation and then sent to the company for sequencing with the following sequencing primer: 5'-GCATATACGATACAAGGCTG-3' (SEQ ID NO.: 129). A total of 38 sequencing-positive colonies were obtained, with a positive rate of 76%.

Strategy (2): Gibson Assembly Method

The homologous arm (sequence at the two ends of the target vector after linearization) was attached to both sides of the sgRNA sequence, and the homologous arm sequence was designed as:

5'-TATCTTGTGGAAAGGACGAAACACCG (SEQ ID NO.: 163)

$N_{20}$GTTTTAGAGCTAGAAATAGCAAGTTAAAAT (SEQ ID NO.: 164)-3' ($N_{20}$ is sgRNA sequence).

Figure 9:
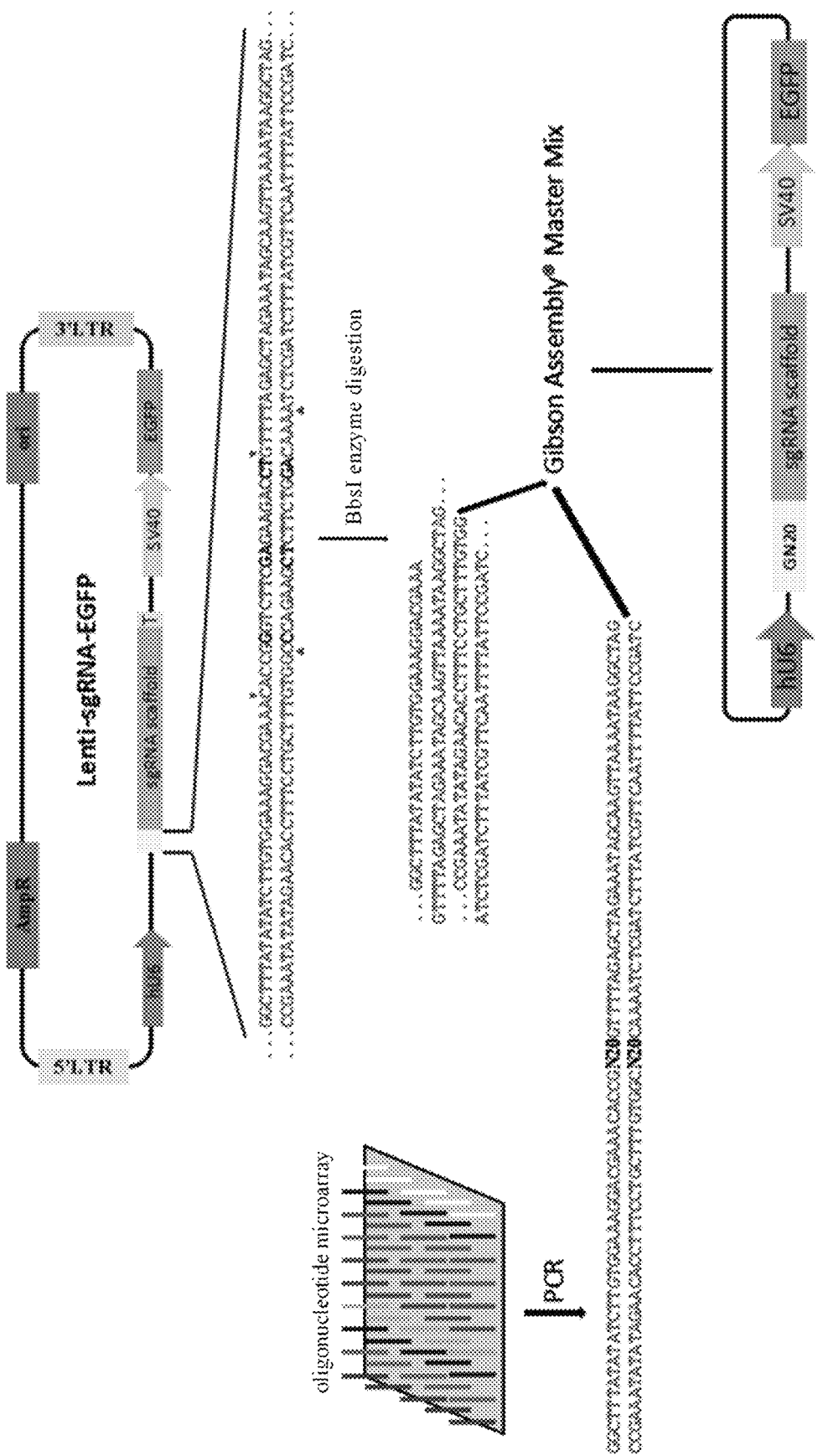
FIG. 9. The schematic diagram of an experiment of Gibson assembly method (scheme 2) in Example 3 of the present invention.

The process of Gibson Assembly for library construction is shown in FIG. 9, and the 85,674-oligonucleotide pool was also synthesized by CustomArray Inc., USA.

An Example of Probes:
>ENSSSCG00000000001_5_592106_592135_m,
TATCTTGTG-
GAAAGGACGAAACACCGTGACGACTCGGCCAC-
CACCAGTTTTAGAGCT AGAAATAGCAAGTTAAAAT
(SEQ ID NO.: 171) (The underlined part is sgRNA).

Then, a library was constructed for the synthetic oligonucleotides, and the oligonucleotide pool was used as a template for PCR amplification with the following amplified primer sequence:

F: 5'-GGCTTTATATATCTTGTG-GAAAGGACGAAACACCG-3' (SEQ ID NO.: 130);

R: 5'-CTAGCCTTATTTTAACTTGCTAT-TTCTAGCTCTAAAAC-3' (SEQ ID NO.:131).

The obtained PCR amplification product was ligated with the target vector by homologous recombination according to the method of the Gibson assembly (NEB, E2611L) kit instructions, followed by transformation of the assembled product into *E. coli* cells for plate culture.

After obtaining transformants, the plasmid was extracted and identified by high throughput sequencing.

Example 4

Assessing the effect of different amounts of Gibson assembly solutions on transformation efficiency The amount of PCR purified product was 60 ng, the amount of lenti-sgRNA-GFP vector after digestion was 100 ng. The amount of *E. coli* used in a transformation reaction was 50 μl, and the amount of Gibson assembly products were 5 μL, 10 μL, and 20 μL, respectively. Finally, the number of clones was counted (Gibson assembly product is the assembly product in Example 3). The statistical results are shown in FIG. 10. When the amount of Gibson assembly product used is 5 μL, a relatively high transformation efficiency can be achieved, with the number of *E. coli* cells being about $0.5 \times 10^9$ in a ligation reaction.

Example 5

Assessing the Effect of Different Amounts of Library Amplification and Purification Products on the Transformation Efficiency In this example, the clones obtained by PCR amplification products using 5 ng~450 ng for ligation transformation were detected to count the number of clones.

As shown in FIG. 11, the number of growing clones was $3.5 \times 10^3$ to $10 \times 10^4$, indicating that the number of recombinant clones obtained by Strategy 2 in Example 3 is higher than that of the Strategy 1 in Example 3).

Similarly, 50 single colonies were randomly selected for expanding culture and sequenced. A total of 48 positive colonies were obtained, with a positive rate of 96%, which is higher than that of Strategy 1.

As shown by the statistical results, when the amount of the library amplification and purification product for a transformation reaction was 10 ng and the Gibson assembly product amount was 5 μL, a very high transformation efficiency can be achieved. Through numerous transformations, a recombinant vector library of sgRNAs was obtained with a coverage of 200×transformants.

Furthermore, the sgRNA coverage in the library was identified by library construction and high-throughput sequencing.

Example 6

Screening the Optimal Primer Pairs for Specific Amplification of Target Fragments of the Whole Genome sgRNA Plasmid Library After constructing a porcine whole genome sgRNA plasmid library using the Gibson Assembly method (Strategy 2) in Example 3, in order to determine the type and abundance of the sgRNA ligated therein, using the plasmid library as a template, the target region containing the sgRNA sequence was first amplified by PCR, where the sgRNA expression vector backbone was *Lenti*-sgRNA-EGFP. A total of 3 forward primers were designed:

```
                                    (SEQ ID NO.: 132)
   lenti-F1: 5'-CTTGTGGAAAGGACGAAACACC-3';

(SEQ ID NO.: 133)
   lenti-F2: 5'-ATATCTTGTGGAAAGGACG-3';

(SEQ ID NO.: 134)
   lenti-F3: 5'-GAAAGTATTTCGATTTCTTGGC-3'.
```

Seven Reverse Primers:

```
                                    (SEQ ID NO.: 135)
   lenti-R1: 5'-CAAGTTGATAACGGACTAGCC-3';

(SEQ ID NO.: 136)
   lenti-R2: 5'-CAGAATTGGCGCACGCGCTAA-3';

(SEQ ID NO.: 137)
   lenti-R3: 5'-GAGCCATTTGTCTGCAGAATTGGC-3';

(SEQ ID NO.: 138)
   lenti-R4: 5'-GGCTAGCGGTACCTCTAGAGCC-3';
```

-continued lenti-R5: 5'-CCACAGGCTAGCGGTACCTCT-3'; (SEQ ID NO.: 139)

lenti-R6: 5'-AAGCACCGACTCGGTGCCA-3'; (SEQ ID NO.: 140)

lenti-R7: 5'-CTTGCTATTTCTAGCTCT-3'. (SEQ ID NO.: 141)

Combinations of (lenti-F1/R1, lenti-F1/R2, lenti-F1/R3, lenti-F1/R4, lenti-F1/R5, lenti-F1/R6, lenti-F1/R7, lenti-F2/R1, lenti-F1/R2, lenti-F1/R3, lenti-F1/R4, lenti-F1/R5, lenti-F1/R6, lenti-F1/R7, lenti-F3/R1, lenti-F3/R2, lenti-F3/R3, lenti-F3/R6, lenti-F3/R7) respectively to test amplification specificity.

After amplification specificity test, 6 primer pairs were shown to be able to amplify the target regions containing the sgRNA sequence, the primer pair sequence was as follows:

(1)

lenti-F1: 5'-CTTGTGGAAAGGACGAAACACC-3', (SEQ ID NO.: 132)

lenti-R1: 5'-CAAGTTGATAACGGACTAGCC-3'; (SEQ IDNO.: 135)

(2)

lenti-F1: 5'-CTTGTGGAAAGGACGAAACACC-3', (SEQ ID NO.: 132)

lenti-R6: 5'-AAGCACCGACTCGGTGCCA-3'; (SEQ ID NO.: 140)

(3)

lenti-F2: 5'-ATATCTTGTGGAAAGGACG-3', (SEQ ID NO.: 133)

lenti-R1: 5'-CAAGTTGATAACGGACTAGCC-3'; (SEQ IDNO.: 135)

(4)

lenti-F2: 5'-ATATCTTGTGGAAAGGACG-3', (SEQ ID NO.: 133)

lenti-R6: 5'-AAGCACCGACTCGGTGCCA-3'; (SEQ ID NO.: 140)

(5)

lenti-F3: 5'-GAAAGTATTTCGATTTCTTGGC-3', (SEQ ID NO.: 134)

lenti-R1: 5'-CAAGTTGATAACGGACTAGCC-3'; (SEQ IDNO.: 135)

(6)

lenti-F3: 5'-GAAAGTATTTCGATTTCTTGGC-3', (SEQ ID NO.: 134)

lenti-R6: 5'-AAGCACCGACTCGGTGCCA-3'. (SEQ ID NO.: 140)

The PCR reaction system: 5×PrimeStar GXL buffer: 2 μL; dNTP ($Mg^{2+}$ plus): 0.8 μL; Forward primer: 0.2 μL; Reverse primer: 0.2 μL; DNA: (20~50) ng; adding water to 10 μL; the reaction procedure: 94° C., 5 min; 28 cycles (98° C., 10 s; 62° C., 15 s; 68° C., 10 s); 68° C., 5 min; 15° C., 2 min.

Figure 12:
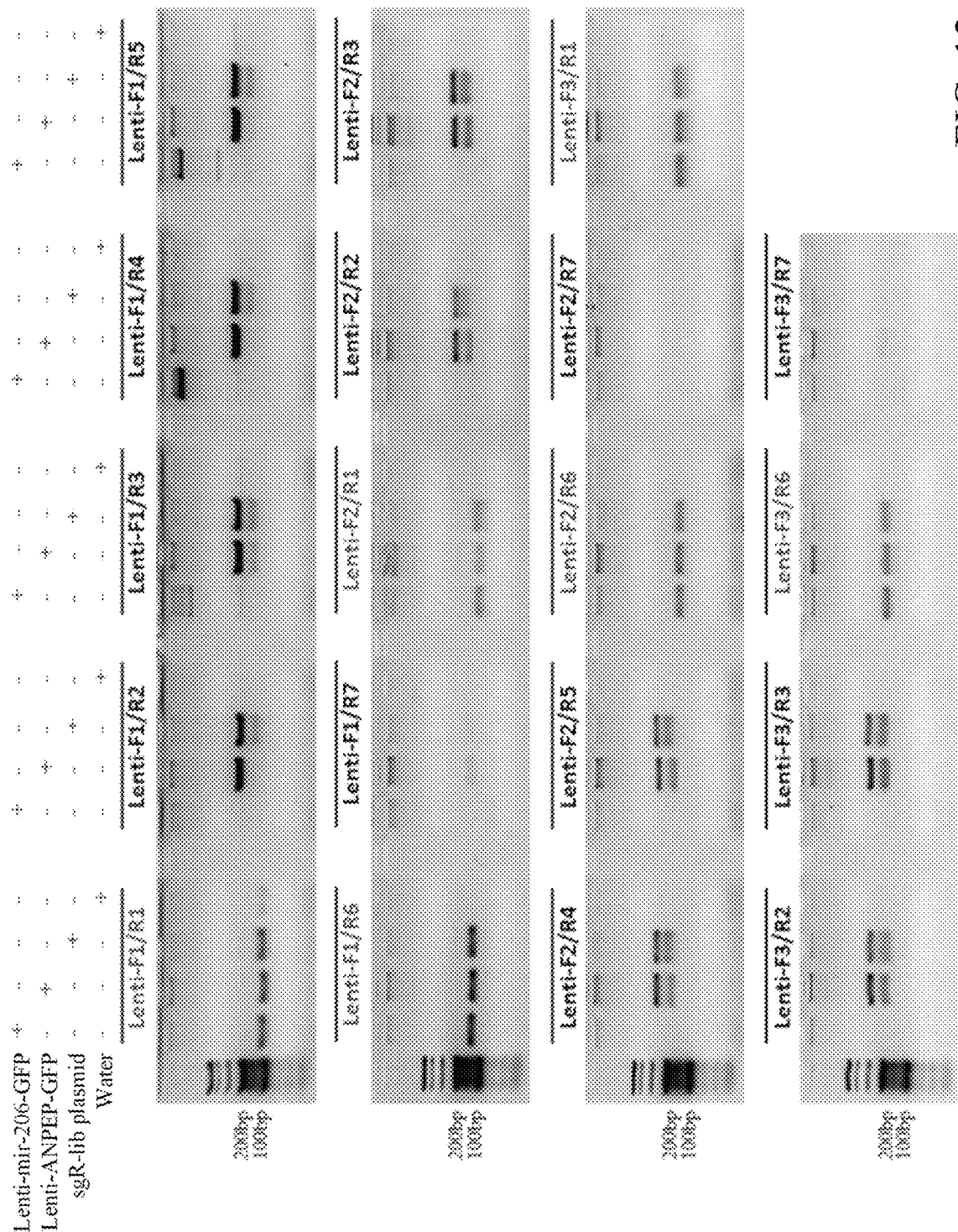
FIG. 12. An optimal primer pair for screening specific amplification of target fragments of the porcine whole genome sgRNA plasmid library in Example 6 of the present invention.

FIG. 12 shows the PCR test results. All the 6 primer pairs can amplify the target regions containing the sgRNA sequence, with three of them being capable of specific amplification, and the amplification sequence is identified by sequencing as the inserted target fragment. Based on this, for the optimal detection results, the combination of the primer pair lenti-F1/R6 or lenti-F3/R6 was preferred, most preferably, lenti-F1/R6.

The PCR products were sent to the company for the construction of a library containing sgRNA sequence regions and high-throughput sequencing analysis was performed. Bioinformatics analysis was performed after the sequencing data was obtained. Finally, it was determined that the plasmid library contained 82,392 sgRNAs, with a coverage rate of 96.17% versus the library designed above (82,392/85674=96.17%), wherein 14,958 protein-coding genes were targeted, 14,168 lincRNAs and 142 miRNAs were targeted, and 970 NTC-sgRNAs as negative controls were contained.

As shown above, Through the method of the present invention, a porcine whole genome CRISPR/Cas9 knockout library with a high coverage can be obtained, and partial sequences of the library are shown in FIG. 16.

Example 7

Figure 13:
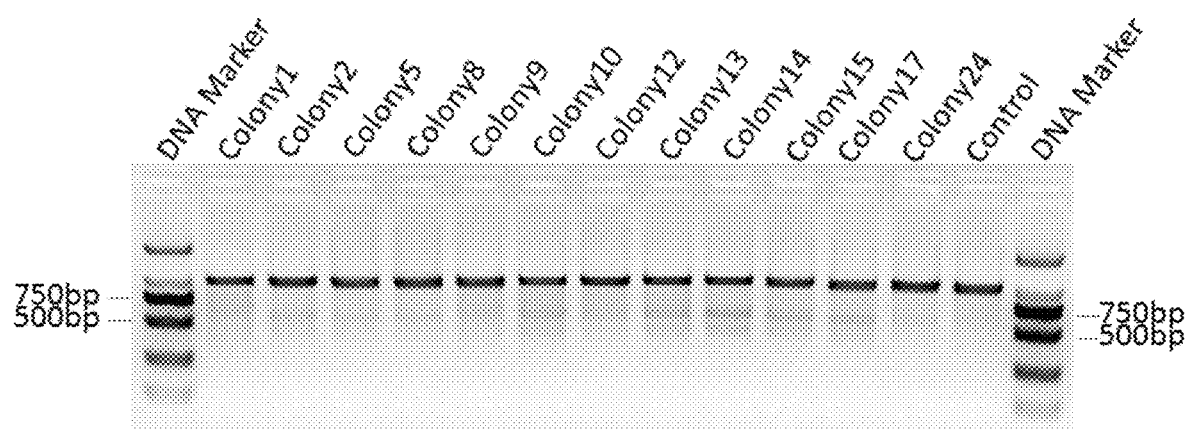
FIG. 13. Construction of a PK-15 cell line stably expressing Cas9 and determination of its activity in Example 7 of the present invention.

Construction of PK-15 Cell Line Stably Expressing Cas9 (PK15-Cas9) and Determination of its Activity Lentivirus Cas9-puromycin was used to infect porcine PK-15 cells, and a cell line stably expressing Cas9 was obtained by puromycin (3 μg/mL) drug screening, followed by transfection with the sgRNA plasmid (Lenti-sgRNA-GFP) targeting the ANPEP gene, the sgRNA sequence: GCAACAGCGTTGTGGGTAGGCGG (SEQ ID NO.: 172) (the underlined part refers to the PAM corresponding to the target sequence binding site targeted by (corresponding to) the sgRNA). At 48 hours post transfection, the cell DNA was extracted and the target fragment was amplified by PCR using the primer pairs: ANPEP-952-F: 5'-CTCCTGCAGCCTGTAACCAGA-3' (SEQ ID NO.: 142); ANPEP-952-R: 5'-AAGGTTC-CAAGGTCCCGAATC-3' (SEQ ID NO.: 143). As shown in FIG. 13, higher activity was found in different clones, and 14 #clone was randomly selected for subsequent experiments.

Example 8

The Activity Test of sgRNA-Expressing Lentivirus Vector

The PK-15-Cas9 cell line was infected with lentiviral sgRNA targeting the ANPEP gene, followed by detecting the GFP expression and sgRNA activity separately at 2, 4, 6, 8, and 10 days post infection. The sgRNA activity was detected by conventional T7E1 digestion experiments, and expressed as percent cleavage activity (Indel %).

Figure 14:
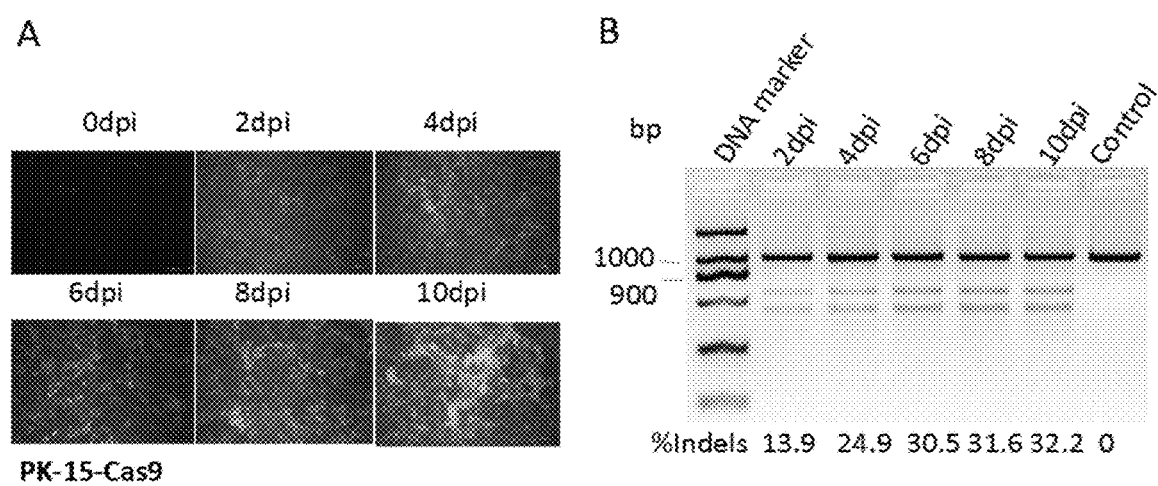
FIG. 14. Test of the activity on sgRNA expressed by the lentivirus vector (A) The sgRNA lentiviral vector activity is indicated by evaluating the expression of GFP fluorescent protein; (B) the detected sgRNA lentiviral vector targeting the ANPEP gene is taken as an example to illustrate that the plasmid system of the library can effectively cut genomic targets.

As shown in FIGS. 14 A and B, lentivirus sgRNA infection can guide Cas9 targeted cleavage. With the increase of infection time, GFP fluorescence gradually increases, the sgRNA activity tends to be stable (about 30%) at 6 dpi.

Example 9

The Activity Test of the Lentiviral sgRNA Library

The PK-15-Cas9 cell line was infected with the lentivirus sgRNA library (MOI=0.3), followed by the inoculation of monoclonal cells. After growth for 7-10 days, monoclonal cell clones expressing GFP were collected in a 12-well cell culture plate. After the cells were full, the cell genomic DNA was extracted, followed by amplification using the primer pairs Lenti-F1: ATATCTTGTGGAAAGGACG (SEQ ID NO.: 133), Lenti-R4: CAAGTTGATAACGGACTAGCC (SEQ ID NO.: 135), with the purpose to amplify sgRNA sequences integrated into the genome, using Primestar GXL Polymerase (Takara, R050A) as the enzyme for the amplification at an annealing temperature of 60° C. and an extension time of 15 s. Then the PCR product was purified and cloned into a PMD19-T vector, followed by sequencing analysis of the selected colonies to identify the sgRNAs stably integrated into the cells. Next, the corresponding genes were determined according to the sgRNA sequence, and primers were designed to amplify the sgRNA target sequences and flanking sequences. Finally, the genome editing efficiency was determined by T7E1 assay.

Sequencing results are shown as follows:

Monoclonal Colony 1:

>ENSSSCG00000021964_16_50164110_50164139_p
(SEQ ID NO.: 156)
5'-cAGCTTGATGAGAAGAGGC-3';

Monoclonal Colony 2:

>ENSSSCG00000005129_1_221066930_221066959_m
(SEQ ID NO.: 157)
5'-GTTCGACCAGGGACTTCTGA-3';

Monoclonal Colony 3:

>ENSSSCG00000005037_1_202467280_202467309_p
(SEQ ID NO.: 158)
5'-GCTTGCAGATTTAATTCCAT-3';

Monoclonal Colony 4:

>ENSSSCT00000021494_62_91_m
(SEQ ID NO.: 159)
5'-GATTTGGTGAGCAAGCTACG-3';

Monoclonal Colony 5:

>ENSSSCG00000003717_6_103771733_103771762_m
(SEQ ID NO.: 160)
5'-TTCATCTTGAAGCTTGGCA-3';

Monoclonal Colony 6:

>ENSSSCG00000013016_2_6384602_6384631_p
(SEQ ID NO.: 161)
5'-ATCCACGTATCTCTTGGCC-3';

Monoclonal Colony 7:

>ANPEP-sgRlib-2
(SEQ ID NO.: 162)
5'-ACCCTACCTCACTCCCAACG.

Figure 15:
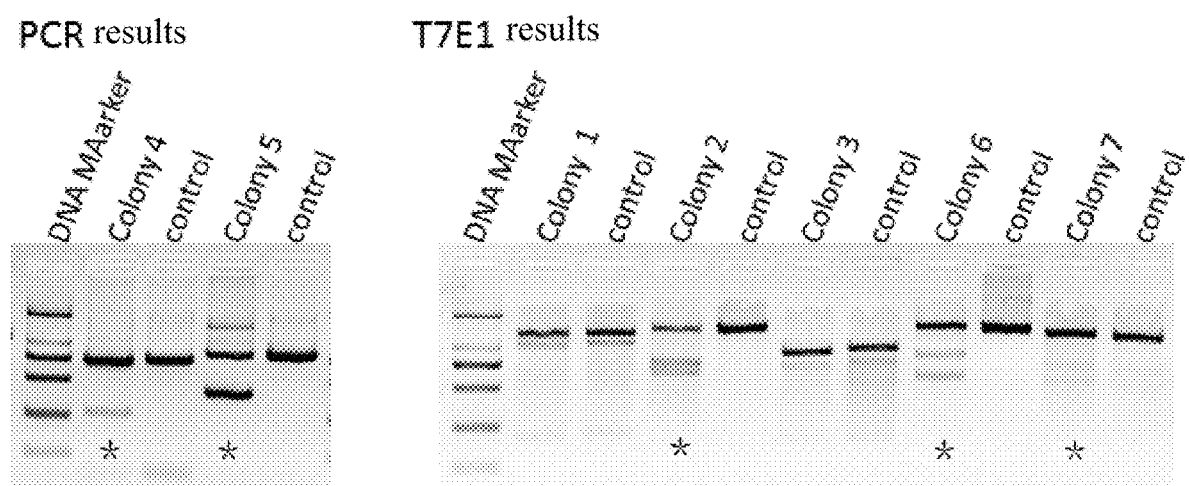
FIG. 15. TesT for screening the mutant cell lines by lentivirus library infection in Example 9 of the present invention. * indicates sgRNA targets with genome editing activity, with large fragment deletion mutations observed from PCR amplification results.

Based on the identified genes, the amplification primers are designed as follows:

(1) Colony 1-1003-F:
(SEQ ID NO.: 144)
5'-TGTTTCCCTCCCTGGCAATTT-3',

Colony1-1003-R:
(SEQ ID NO.: 145)
5'-TTGCCGCTGTCTCGGTAGAA-3';

(2) Colony2-1166-F:
(SEQ ID NO.: 146)
5'-AGGAGAGGTGCGGGAATGT-3',

Colony2-1166-R:
(SEQ ID NO.: 147)
5'-TACTTGCTTTGGGAAATACAGGC-3';

(3) Colony3-722-F:
(SEQ ID NO.: 148)
5'-GGTGCAAATATCAAGCCAGCA-3',

Colony3-722-R:
(SEQ ID NO.: 149)
5'-CAGACTGTGGCAATTGACTGT-3';

(4) Colony4-743-F:
(SEQ ID NO.: 150)
5'-ACCTGTGACTATCCTTCAGCAC-3',

Colony4-743-R:
(SEQ ID NO.: 151)
5'-AACAGCTAACCTCCAGGCAC-3';

(5) Colony5-864-F:
(SEQ ID NO.: 152)
5'-GGAGTGGTTCTTCTTGCTCCA-3',

Colony5-864-R:
(SEQ ID NO.: 153)
5'-ATCCTGGTTTACAGAGTTGTGA-3';

(6) Colony6-1110-F:
(SEQ ID NO.: 154)
5'-AGTCTCAGCTACCAGGCCATA-3',

Colony6-1110-R:
(SEQ ID NO.: 155)
5'-TGTTCAGGCAGAGATCACCA-3';

(7) Colony7-952-F:
(SEQ ID NO.: 142)
5'-CTCCTGCAGCCTGTAACCAGA-3',

Colony7-952-R:
(SEQ ID NO.: 143)
5'-AAGGTTCCAAGGTCCCGAATC-3';

After PCR amplification of the target fragments, it was recovered using the PCR product purification and recovery kit according to the instructions and it was digested by T7EN1 assay. In FIG. 15, it is shown that the target sites of 5 cell clones were cleaved, with large fragment sequence deletion in the target observed in two of them. The research results show that the porcine sgRNA library in the present invention can be used to construct a mutant cell library and can also be used for whole genome functional gene screening.

All documents mentioned in the present invention are incorporated as reference in this application, just as each article was cited individually as a reference. Additionally, it should be understood that various changes or modifications can be made to the present invention, and these equivalents also fall within the scope defined by the claims appended hereto.

What is claimed is:

1. A porcine whole genome-specific sgRNA library, wherein the library includes:
   (i) N kinds of vectors expressing porcine-specific sgRNA, wherein N is a positive integer ≥20,000, and the porcine-specific sgRNA is a target gene for the porcine whole genome and the target gene is selected from the group consisting of: (a) a protein encoding gene, (b) a lincRNA, (c) a miRNA and (d) a combination of (a), (b) and (c);
   in addition, the porcine-specific sgRNA has the following structural characteristics:
   (1) the target gene locus targeted by the sgRNA contains PAM as NGG (wherein N is any base of A, T, C, G);
   (2) the length of sgRNA is 19 or 20 nt;
   (3) the GC content of sgRNA is 40-60%;
   (4) a whole-genome off-target evaluation of sgRNA selects off-target sites that do not contain 1 and 2 base mismatches, compared with other sgRNAs, sgRNAs with a smallest number of off-targets are selected;
   (5) for a porcine-specific sgRNA that targets a protein-coding gene, the binding position thereof is located in a region 500 bp downstream of the start codon ATG of the coding gene; for a porcine-specific sgRNA that targets a lincRNA gene, the binding position thereof is located in a 500 bp region downstream of the lincRNA transcription start point; for a porcine-specific sgRNA that targets a miRNA gene, the binding position thereof is a miRNA precursor sequence or a mature sequence; and (ii) optionally, M kinds of negative control vectors, which are the vectors expressing unrelated sgRNA, wherein M is a positive integer.

2. The sgRNA library of claim 1, wherein the expression vector contains an expression cassette expressing porcine sgRNA, having a structure from 5' to 3' shown by Formula I:

$$Z_0\text{-}Z_1\text{-}Z_2 \qquad (I)$$

wherein Z0 is a first promoter;

Z1 is AL-$N_{20}$-AR, wherein AL is a left arm sequence upstream of the coding sequence of porcine-specific sgRNA; $N_{20}$ is a coding sequence of porcine-specific sgRNA; AR is a right arm sequence downstream of the coding sequence of porcine-specific sgRNA;

Z2 is a sgRNA scaffold sequence.

3. The sgRNA library of claim 2, wherein the expression cassette has a structure from 5' to 3' shown in Formula II:

Z0-Z1-Z2-L-Z3-Z4      (II)

wherein Z0, Z1, and Z2 are as described above,

L is an optional interval sequence;

Z3 is a second promoter;

Z4 is a reporter gene.

4. The sgRNA library of claim 2, wherein the first promoter is a promoter that starts sgRNA expression.

5. The sgRNA library of claim 3, wherein the second promoter is selected from the group consisting of: a CMV promoter, a CAG promoter, a CBh promoter, a tissue-specific promoter, and a combination thereof.

6. The sgRNA library of claim 2, wherein Z1 has a structure of formula (IV):

5'-TATCTTGTGGAAAGGACGAAACACCG (SEQ ID NO: 163) $N_{20}$GTTTTAGAGCTAGAAATAGCAAGTTAAAAT (SEQ ID NO: 164)-3', wherein $N_{20}$ is a coding sequence of a porcine-specific sgRNA.

7. A kit containing:

(a) a first container and a porcine whole genome-specific sgRNA library of claim 1 located in the container; and (b) the instructions describing the instructions for using the porcine whole genome-specific sgRNA library.

8. The kit of claim 7, wherein the kit further includes:

(c) a second container and a porcine cell located in the second container, the porcine cell contains a constitutive or inducible protein expressing Cas9.

\* \* \* \* \*

SEQUENCE LISTING

<160> NUMBER OF SEQ ID NOS: 172

<210> SEQ ID NO 1
<211> LENGTH: 23

```
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 1
gacacatatc cacgcagaga ggg                                              23

<210> SEQ ID NO 2
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 2
acacatatcc acgcagagag gg                                               22

<210> SEQ ID NO 3
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 3
cacatatcca cgcagagagg g                                                21

<210> SEQ ID NO 4
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 4
acatatccac gcagagaggg                                                  20

<210> SEQ ID NO 5
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 5
tgctttggtg tggagggtca tgg                                              23

<210> SEQ ID NO 6
<211> LENGTH: 22
<212> TYPE: DNA
<213> ORGANISM: artificial sequence
<220> FEATURE:
<223> OTHER INFORMATION: synthesized
```

```
<220> FEATURE:
<221> NAME/KEY: misc_feature
<223> OTHER INFORMATION: sgRNA

<400> SEQUENCE: 6
gctttggtgt ggagggtcat gg                                              22

<210> SEQ ID NO 7
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 7
ctttggtgtg gagggtcatg g                                               21

<210> SEQ ID NO 8
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 8
tttggtgtgg agggtcatgg                                                 20

<210> SEQ ID NO 9
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 9
ctcatggcaa caccagtcga tgg                                             23

<210> SEQ ID NO 10
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 10
tcatggcaac accagtcgat gg                                              22

<210> SEQ ID NO 11
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA
```

<400> SEQUENCE: 11
catggcaaca ccagtcgatg g                                              21

<210> SEQ ID NO 12
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 12
atggcaacac cagtcgatgg                                                20

<210> SEQ ID NO 13
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 13
ggaggtgctg gcagctgctg cgg                                            23

<210> SEQ ID NO 14
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 14
gaggtgctgg cagctgctgc gg                                             22

<210> SEQ ID NO 15
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 15
aggtgctggc agctgctgcg g                                              21

<210> SEQ ID NO 16
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 16
ggtgctggca gctgctgcgg                                                20

```
<210> SEQ ID NO 17
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 17
gaaaatgttt cctgactcag agg                                          23

<210> SEQ ID NO 18
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 18
aaaatgtttc ctgactcaga gg                                           22

<210> SEQ ID NO 19
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 19
aaatgtttcc tgactcagag g                                            21

<210> SEQ ID NO 20
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 20
aatgtttcct gactcagagg                                              20

<210> SEQ ID NO 21
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 21
ccacccggat ggagttgcag cgg                                          23

<210> SEQ ID NO 22
<211> LENGTH: 22
<212> TYPE: DNA
```

```
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 22
cacccggatg gagttgcagc gg                                              22

<210> SEQ ID NO 23
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 23
acccggatgg agttgcagcg g                                               21

<210> SEQ ID NO 24
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 24
cccggatgga gttgcagcgg                                                 20

<210> SEQ ID NO 25
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 25
aagaaaatgt ggaaaaagag ggg                                             23

<210> SEQ ID NO 26
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 26
agaaaatgtg gaaaagagg gg                                               22

<210> SEQ ID NO 27
<211> LENGTH: 21
<212> TYPE: DNA
<213> ORGANISM: artificial sequence
<220> FEATURE:
<223> OTHER INFORMATION: synthesized
<220> FEATURE:
```

```
<221> NAME/KEY: misc_feature
<223> OTHER INFORMATION: sgRNA

<400> SEQUENCE: 27
gaaaatgtgg aaaaagaggg g                                          21

<210> SEQ ID NO 28
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 28
aaaatgtgga aaaagagggg                                            20

<210> SEQ ID NO 29
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 29
atggaatgta aggaagtgtg tgg                                        23

<210> SEQ ID NO 30
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 30
tggaatgtaa ggaagtgtgt gg                                         22

<210> SEQ ID NO 31
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 31
ggaatgtaag gaagtgtgtg g                                          21

<210> SEQ ID NO 32
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 32
```
gaatgtaagg aagtgtgtgg                                        20

<210> SEQ ID NO 33
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 33
attggaagaa cttgcccacg ggg                                    23

<210> SEQ ID NO 34
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 34
ttggaagaac ttgcccacgg gg                                     22

<210> SEQ ID NO 35
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 35
tggaagaact tgcccacggg g                                      21

<210> SEQ ID NO 36
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: sgRNA

<400> SEQUENCE: 36
ggaagaactt gcccacgggg                                        20

<210> SEQ ID NO 37
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 37
caccgacaca tatccacgca gaga                                   24

```
<210> SEQ ID NO 38
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 38
aaactctctg cgtggatatg tgtc                                              24

<210> SEQ ID NO 39
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 39 cacccacacat atccacgcag aga                                              23

<210> SEQ ID NO 40
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 40
aaactctctg cgtggatatg tgt                                               23

<210> SEQ ID NO 41
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 41
cacccacata tccacgcaga ga                                                22

<210> SEQ ID NO 42
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 42
aaactctctg cgtggatatg tg                                                22

<210> SEQ ID NO 43
<211> LENGTH: 21
<212> TYPE: DNA
<213> ORGANISM: artificial sequence
```

```
<220> FEATURE:
<223> OTHER INFORMATION: synthesized
<220> FEATURE:
<221> NAME/KEY: misc_feature
<223> OTHER INFORMATION: primer

<400> SEQUENCE: 43
caccacatat ccacgcagag a                                        21

<210> SEQ ID NO 44
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 44
aaactctctg cgtggatatg t                                        21

<210> SEQ ID NO 45
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 45
cacctgcttt ggtgtggagg gtca                                     24

<210> SEQ ID NO 46
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 46
aaactgaccc tccacaccaa agca                                     24

<210> SEQ ID NO 47
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 47
caccgctttg gtgtggaggg tca                                      23

<210> SEQ ID NO 48
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
```

<223> OTHER INFORMATION: primer

<400> SEQUENCE: 48
aaactgaccc tccacaccaa agc                                          23

<210> SEQ ID NO 49
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 49 cacccttttgg tgtggagggt ca                                          22

<210> SEQ ID NO 50
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 50
aaactgaccc tccacaccaa ag                                           22

<210> SEQ ID NO 51
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 51 caccttttggt gtggagggtc a                                           21

<210> SEQ ID NO 52
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 52
aaactgaccc tccacaccaa a                                            21

<210> SEQ ID NO 53
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 53
caccctcatg gcaacaccag tcga                                              24

<210> SEQ ID NO 54
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 54
aaactcgact ggtgttgcca tgag                                              24

<210> SEQ ID NO 55
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 55
cacctcatgg caacaccagt cga                                               23

<210> SEQ ID NO 56
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 56
aaactcgact ggtgttgcca tga                                               23

<210> SEQ ID NO 57
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 57
cacccatggc aacaccagtc ga                                                22

<210> SEQ ID NO 58
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 58
aaactcgact ggtgttgcca tg                                                22

<210> SEQ ID NO 59

```
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 59
caccatggca acaccagtcg a                                              21

<210> SEQ ID NO 60
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 60
aaactcgact ggtgttgcca t                                              21

<210> SEQ ID NO 61
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 61
caccggaggt gctggcagct gctg                                           24

<210> SEQ ID NO 62
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 62
aaaccagcag ctgccagcac ctcc                                           24

<210> SEQ ID NO 63
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 63
caccgaggtg ctggcagctg ctg                                            23

<210> SEQ ID NO 64
<211> LENGTH: 23
<212> TYPE: DNA
<213> ORGANISM: artificial sequence
<220> FEATURE:
```

```
<223> OTHER INFORMATION: synthesized
<220> FEATURE:
<221> NAME/KEY: misc_feature
<223> OTHER INFORMATION: primer

<400> SEQUENCE: 64
aaaccagcag ctgccagcac ctc                                           23

<210> SEQ ID NO 65
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 65
caccaggtgc tggcagctgc tg                                            22

<210> SEQ ID NO 66
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 66
aaaccagcag ctgccagcac ct                                            22

<210> SEQ ID NO 67
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 67
caccggtgct ggcagctgct g                                             21

<210> SEQ ID NO 68
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 68
aaaccagcag ctgccagcac c                                             21

<210> SEQ ID NO 69
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer
```

```
<400> SEQUENCE: 69
caccgaaaat gtttcctgac tcag                                          24

<210> SEQ ID NO 70
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 70
aaacctgagt caggaaacat tttc                                          24

<210> SEQ ID NO 71
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 71
caccaaaatg tttcctgact cag                                           23

<210> SEQ ID NO 72
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 72
aaacctgagt caggaaacat ttt                                           23

<210> SEQ ID NO 73
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 73
caccaaatgt ttcctgactc ag                                            22

<210> SEQ ID NO 74
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 74
aaacctgagt caggaaacat tt                                            22
```

```
<210> SEQ ID NO 75
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 75
caccaatgtt tcctgactca g                                              21

<210> SEQ ID NO 76
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 76
aaacctgagt caggaaacat t                                              21

<210> SEQ ID NO 77
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 77
caccccaccc ggatggagtt gcag                                           24

<210> SEQ ID NO 78
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 78
aaacctgcaa ctccatccgg gtgg                                           24

<210> SEQ ID NO 79
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 79
cacccacccg gatggagttg cag                                            23

<210> SEQ ID NO 80
<211> LENGTH: 23
```

```
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 80
aaacctgcaa ctccatccgg gtg                                             23

<210> SEQ ID NO 81
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 81
caccacccgg atggagttgc ag                                              22

<210> SEQ ID NO 82
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 82
aaacctgcaa ctccatccgg gt                                              22

<210> SEQ ID NO 83
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 83 caccccccgga tggagttgca g                                              21

<210> SEQ ID NO 84
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 84
aaacctgcaa ctccatccgg g                                               21

<210> SEQ ID NO 85
<211> LENGTH: 24
<212> TYPE: DNA
<213> ORGANISM: artificial sequence
<220> FEATURE:
<223> OTHER INFORMATION: synthesized
```

```
<220> FEATURE:
<221> NAME/KEY: misc_feature
<223> OTHER INFORMATION: primer

<400> SEQUENCE: 85
caccaagaaa atgtggaaaa agag                                          24

<210> SEQ ID NO 86
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 86
aaacctcttt ttccacattt tctt                                          24

<210> SEQ ID NO 87
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 87
caccagaaaa tgtggaaaaa gag                                           23

<210> SEQ ID NO 88
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 88
aaacctcttt ttccacattt tct                                           23

<210> SEQ ID NO 89
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 89
caccgaaaat gtggaaaaag ag                                            22

<210> SEQ ID NO 90
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer
```

```
<400> SEQUENCE: 90
aaacctcttt ttccacattt tc                                          22

<210> SEQ ID NO 91
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 91
caccaaaatg tggaaaaaga g                                           21

<210> SEQ ID NO 92
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 92
aaacctcttt ttccacattt t                                           21

<210> SEQ ID NO 93
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 93
caccatggaa tgtaaggaag tgtg                                        24

<210> SEQ ID NO 94
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 94
aaaccacact tccttacatt ccat                                        24

<210> SEQ ID NO 95
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 95
cacctggaat gtaaggaagt gtg                                         23
```

<210> SEQ ID NO 96
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 96
aaaccacact tccttacatt cca                                    23

<210> SEQ ID NO 97
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 97
caccggaatg taaggaagtg tg                                     22

<210> SEQ ID NO 98
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 98
aaaccacact tccttacatt cc                                     22

<210> SEQ ID NO 99
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 99
caccgaatgt aaggaagtgt g                                      21

<210> SEQ ID NO 100
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 100
aaaccacact tccttacatt c                                      21

<210> SEQ ID NO 101
<211> LENGTH: 24
<212> TYPE: DNA

```
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 101
caccattgga agaacttgcc cacg                                              24

<210> SEQ ID NO 102
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 102
aaaccgtggg caagttcttc caat                                              24

<210> SEQ ID NO 103
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 103
caccttggaa gaacttgccc acg                                               23

<210> SEQ ID NO 104
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 104
aaaccgtggg caagttcttc caa                                               23

<210> SEQ ID NO 105
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 105
cacctggaag aacttgccca cg                                                22

<210> SEQ ID NO 106
<211> LENGTH: 22
<212> TYPE: DNA
<213> ORGANISM: artificial sequence
<220> FEATURE:
<223> OTHER INFORMATION: synthesized
<220> FEATURE:
```

<221> NAME/KEY: misc_feature
<223> OTHER INFORMATION: primer

<400> SEQUENCE: 106
aaaccgtggg caagttcttc ca                                    22

<210> SEQ ID NO 107
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 107
caccggaaga acttgcccac g                                     21

<210> SEQ ID NO 108
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 108
aaaccgtggg caagttcttc c                                     21

<210> SEQ ID NO 109
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 109
tcacccaatg ccagtgagat                                       20

<210> SEQ ID NO 110
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 110
tatctccagg agcacagcca                                       20

<210> SEQ ID NO 111
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 111
ctggatccgt ctttcgcgtt                                              20

<210> SEQ ID NO 112
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 112
gctcgttctc caggtagtag g                                            21

<210> SEQ ID NO 113
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 113
tgaaactggg ctgctgcata                                              20

<210> SEQ ID NO 114
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 114
aaccacgact agaggctgac                                              20

<210> SEQ ID NO 115
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 115
gccgtccaag acctaccga                                               19

<210> SEQ ID NO 116
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 116
atgctccaac gcctccaca                                               19

```
<210> SEQ ID NO 117
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 117
aagggagttg ggaatagggt g                                              21

<210> SEQ ID NO 118
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 118 aggggactg tagatgggtg a                                               21

<210> SEQ ID NO 119
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 119
ggcattctac ctcagcaacc                                                20

<210> SEQ ID NO 120
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 120
aacctccctc cctgtaacc                                                 19

<210> SEQ ID NO 121
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 121
agattcactg gtgtggcaag                                                20

<210> SEQ ID NO 122
<211> LENGTH: 21
<212> TYPE: DNA
<213> ORGANISM: artificial sequence
```

```
<220> FEATURE:
<223> OTHER INFORMATION: synthesized
<220> FEATURE:
<221> NAME/KEY: misc_feature
<223> OTHER INFORMATION: primer

<400> SEQUENCE: 122
gattgtttcc gttgtagcgt g                                              21

<210> SEQ ID NO 123
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 123
gagtggctct ctgcgtgaat                                                20

<210> SEQ ID NO 124
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 124
gcttccttgg tgagggagtc                                                20

<210> SEQ ID NO 125
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 125
taacacggct ctctctgtgc                                                20

<210> SEQ ID NO 126
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 126
gagtagcctg tttcggggag                                                20

<210> SEQ ID NO 127
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
```

<223> OTHER INFORMATION: primer

<400> SEQUENCE: 127
acaggcccaa gatcgtgaa                                    19

<210> SEQ ID NO 128
<211> LENGTH: 18
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 128
ctccttgcgc ttcttgga                                     18

<210> SEQ ID NO 129
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 129
gcatatacga tacaaggctg                                   20

<210> SEQ ID NO 130
<211> LENGTH: 35
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 130
ggctttatat atcttgtgga aaggacgaaa caccg                  35

<210> SEQ ID NO 131
<211> LENGTH: 38
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 131
ctagccttat tttaacttgc tatttctagc tctaaaac               38

<210> SEQ ID NO 132
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 132
cttgtggaaa ggacgaaaca cc                                                22

<210> SEQ ID NO 133
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 133
atatcttgtg gaaaggacg                                                    19

<210> SEQ ID NO 134
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 134
gaaagtattt cgatttcttg gc                                                22

<210> SEQ ID NO 135
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 135
caagttgata acggactagc c                                                 21

<210> SEQ ID NO 136
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 136
cagaattggc gcacgcgcta a                                                 21

<210> SEQ ID NO 137
<211> LENGTH: 24
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 137
gagccatttg tctgcagaat tggc                                              24

<210> SEQ ID NO 138

```
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 138
ggctagcggt acctctagag cc                                              22

<210> SEQ ID NO 139
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 139
ccacaggcta gcggtacctc t                                               21

<210> SEQ ID NO 140
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 140
aagcaccgac tcggtgcca                                                  19

<210> SEQ ID NO 141
<211> LENGTH: 18
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 141
cttgctattt ctagctct                                                   18

<210> SEQ ID NO 142
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 142
ctcctgcagc ctgtaaccag a                                               21

<210> SEQ ID NO 143
<211> LENGTH: 21
<212> TYPE: DNA
<213> ORGANISM: artificial sequence
<220> FEATURE:
```

```
<223> OTHER INFORMATION: synthesized
<220> FEATURE:
<221> NAME/KEY: misc_feature
<223> OTHER INFORMATION: primer

<400> SEQUENCE: 143
aaggttccaa ggtcccgaat c                                              21

<210> SEQ ID NO 144
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 144
tgtttccctc cctggcaatt t                                              21

<210> SEQ ID NO 145
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 145
ttgccgctgt ctcggtagaa                                                20

<210> SEQ ID NO 146
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 146
aggagaggtg cgggaatgt                                                 19

<210> SEQ ID NO 147
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 147
tacttgcttt gggaaataca ggc                                            23

<210> SEQ ID NO 148
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer
```

```
<400> SEQUENCE: 148
ggtgcaaata tcaagccagc a                                              21

<210> SEQ ID NO 149
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 149
cagactgtgg caattgactg t                                              21

<210> SEQ ID NO 150
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 150
acctgtgact atccttcagc ac                                             22

<210> SEQ ID NO 151
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 151
aacagctaac ctccaggcac                                                20

<210> SEQ ID NO 152
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 152
ggagtggttc ttcttgctcc a                                              21

<210> SEQ ID NO 153
<211> LENGTH: 22
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 153
atcctggttt acagagttgt ga                                             22
```

<210> SEQ ID NO 154
<211> LENGTH: 21
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 154
agtctcagct accaggccat a                                              21

<210> SEQ ID NO 155
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 155
tgttcaggca gagatcacca                                                20

<210> SEQ ID NO 156
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 156
cagcttgatg agaagaggc                                                 19

<210> SEQ ID NO 157
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 157
gttcgaccag ggacttctga                                                20

<210> SEQ ID NO 158
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 158
gcttgcagat ttaattccat                                                20

<210> SEQ ID NO 159
<211> LENGTH: 20

```
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 159
gatttggtga gcaagctacg                                            20

<210> SEQ ID NO 160
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 160
ttcatcttga agcttggca                                             19

<210> SEQ ID NO 161
<211> LENGTH: 19
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 161
atccacgtat ctcttggcc                                             19

<210> SEQ ID NO 162
<211> LENGTH: 20
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 162
accctacctc actcccaacg                                            20

<210> SEQ ID NO 163
<211> LENGTH: 26
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: homologous arm

<400> SEQUENCE: 163
tatcttgtgg aaaggacgaa acaccg                                     26

<210> SEQ ID NO 164
<211> LENGTH: 30
<212> TYPE: DNA
<213> ORGANISM: artificial sequence
<220> FEATURE:
<223> OTHER INFORMATION: synthesized
```

```
<220> FEATURE:
<221> NAME/KEY: misc_feature
<223> OTHER INFORMATION: homologous arm

<400> SEQUENCE: 164
gttttagagc tagaaatagc aagttaaaat                                    30

<210> SEQ ID NO 165
<211> LENGTH: 82
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: the sgRNA scaffold sequence

<400> SEQUENCE: 165
gttttagagc tagaaatagc aagttaaaat aaggctagtc cgttatcaac ttgaaaaagt   60
ggcaccgagt cggtgctttt tt                                            82

<210> SEQ ID NO 166
<211> LENGTH: 32
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: a PCR amplified linker sequence

<400> SEQUENCE: 166
acaggcccaa gatcgtgaag aagacagcac cg                                 32

<210> SEQ ID NO 167
<211> LENGTH: 28
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: a PCR amplified linker sequence

<400> SEQUENCE: 167
gtttctgtct tccaagaagc gcaaggag                                      28

<210> SEQ ID NO 168
<211> LENGTH: 32
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: a PCR amplified linker sequence

<400> SEQUENCE: 168
tgtccgggtt ctagcacttc ttctgtcgtg gc                                 32

<210> SEQ ID NO 169
<211> LENGTH: 30
<212> TYPE: DNA
<213> ORGANISM: artificial sequence
<220> FEATURE:
<223> OTHER INFORMATION: synthesized
<220> FEATURE:
<221> NAME/KEY: misc_feature
```

```
<223> OTHER INFORMATION: a PCR amplified linker sequence

<400> SEQUENCE: 169
caaagacaga agaggttctt cgcgttcctc                                    30

<210> SEQ ID NO 170
<211> LENGTH: 82
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: probe

<400> SEQUENCE: 170
acaggcccaa gatcgtgaag aagacagcac cgcacgacgt agtagaagcg cagtttctgt    60
cttctccaag aagcgcaagg ag                                            82

<210> SEQ ID NO 171
<211> LENGTH: 76
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: probe

<400> SEQUENCE: 171
tatcttgtgg aaaggacgaa acaccgtgac gactcggcca ccaccagttt tagagctaga    60
aatagcaagt taaaat                                                   76

<210> SEQ ID NO 172
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: the sgRNA sequence

<400> SEQUENCE: 172
gcaacagcgt tgtgggtagg cgg                                           23
```